(12) United States Patent
Worzel et al.

(10) Patent No.: US 9,234,245 B2
(45) Date of Patent: Jan. 12, 2016

(54) PROGNOSTIC SIGNATURE FOR COLORECTAL CANCER RECURRENCE

(75) Inventors: William P. Worzel, Milan, MI (US); Peter F. Lenehan, Chelsea, MI (US); Arpit Almal, Gujarat (IN); David W. Fry, Ypsilanti, MI (US)

(73) Assignee: Everist Genomics, Inc., Ann Arbor, MI (US)

( * ) Notice: Subject to any disclaimer, the term of this patent is extended or adjusted under 35 U.S.C. 154(b) by 206 days.

(21) Appl. No.: 13/351,485

(22) Filed: Jan. 17, 2012

(65) Prior Publication Data

US 2012/0185174 A1      Jul. 19, 2012

Related U.S. Application Data

(60) Provisional application No. 61/433,798, filed on Jan. 18, 2011.

(51) Int. Cl.
    *C07H 21/04*      (2006.01)
    *C07H 21/02*      (2006.01)
    *C12Q 1/68*      (2006.01)

(52) U.S. Cl.
    CPC ........ *C12Q 1/6886* (2013.01); *C12Q 2600/158* (2013.01)

(58) Field of Classification Search
    CPC ........... C12Q 1/6886; C12Q 2600/118; C12Q 2600/156; C12Q 2600/158; C12Q 1/34; C12Q 1/6809; C12Q 2600/106; C12Q 2600/112; C12Q 2600/136; C12Q 2537/16; C12Q 2545/101; C12Q 2565/626; C12Q 2565/631; C12Q 1/6837; C12Q 2600/178; C12Q 2563/179; G01N 33/6893; G01N 2800/52; G01N 2333/475; G01N 33/74
See application file for complete search history.

(56) References Cited

U.S. PATENT DOCUMENTS

| | | | |
|---|---|---|---|
| 2001/0053519 A1* | 12/2001 | Fodor et al. | 435/6 |
| 2002/0068277 A1* | 6/2002 | Simpson et al. | 435/6 |
| 2004/0215011 A1* | 10/2004 | Deggerdal et al. | 536/25.4 |
| 2006/0257902 A1 | 11/2006 | Mendoza et al. | |

FOREIGN PATENT DOCUMENTS

| | | |
|---|---|---|
| WO | 2005085861 A3 | 9/2005 |
| WO | 2006071983 A3 | 7/2006 |
| WO | 2008021290 A2 | 2/2008 |
| WO | 2010109168 A2 | 9/2010 |

OTHER PUBLICATIONS

Watanabe et al. Cancer Jan. 15, 2009 vol. 115 pp. 283-292.*
Illumina Data Sheet for HumanHT-12 v3 Expression Bead Chip Pub No. 470-2008-005 May 27, 2008.*
Transmittal of the International Search Report and the Written Opinion of the International Application No. PCT/US2012/021539, Mailed May 24, 2012.

* cited by examiner

*Primary Examiner* — Amanda Haney
(74) *Attorney, Agent, or Firm* — Dykema Gossett PLLC

(57) ABSTRACT

An assay system is useful for predicting recurrence and/or non-recurrence of colorectal cancer in a patient. The assay system is adapted to analyze a patient sample for quantitative expression of a prognostic genetic profile correlated with colorectal cancer recurrence. The profile includes the expression of the nucleic acid sequences of SEQ ID NOS: 1, 2, 3, 4, and 5.

4 Claims, 1 Drawing Sheet

PROGNOSTIC SIGNATURE FOR COLORECTAL CANCER RECURRENCE

CROSS REFERENCE TO RELATED APPLICATION

This application claims priority to provisional U.S. patent application entitled "5-GENE PROGNOSTIC SIGNATURE FOR COLORECTAL CANCER RECURRENCE," filed Jan. 18, 2011, having Ser. No. 61/433,798, the disclosure of which is hereby incorporated by reference in its entirety.

FIELD OF THE INVENTION

The present invention generally relates to diagnostic tests. More particularly, the present invention pertains to a diagnostic test for a signature associated with colorectal cancer.

BACKGROUND OF THE INVENTION

Colorectal cancer is the third most commonly diagnosed cancer in the United States, with around 150,000 cases diagnosed each year, and is also the third largest cause of cancer-related deaths. A quarter of patients treated for node-negative colorectal cancer by surgery alone are thought to be "cured" but will experience recurrence within five years. Currently, National Comprehensive Cancer Network (NCCN) Clinical Practice Guidelines are used to predict the risk of recurrence in colorectal cancer patients. Improved techniques for identifying patients at higher risk of cancer recurrence are needed to achieve better treatment plans and patient outcomes by better prediction of risk than that provided by the NCCN Guidelines.

SUMMARY

The foregoing needs are met, to a great extent, by the present invention, wherein in one respect a diagnostic test is disclosed that improves prediction of colorectal cancer reoccurrence at least to some extent.

The invention provides prognostic biomarker genes useful for predicting a likelihood of colorectal cancer recurrence and/or non-recurrence in a patient. In particular, specific genes have been identified by genetic programming analysis as important in the prediction of colorectal cancer recurrence and non-recurrence. These prognostic biomarker genes provide a basis for generating prognostic rules (algorithms) using supervised learning techniques. The generated prognostic rules are applied, for example, by machine-readable software comprising the prognostic rule, to the prediction of risk of recurrence and/or non-recurrence of colorectal cancer in an individual subject.

An exemplary prognostic rule based on levels of expression of the identified prognostic biomarker genes BMI1, ETV6, H3F3B, RPS10, and VEGFA was generated using, Genetic Programming in a supervised learning mode. This rule, and others that may be generated from these identified prognostic biomarker genes by subsequent application of various supervised learning techniques such as Genetic Programming, CART analysis, Support Vector Machine, and Linear Discriminant Analysis, provide useful tools for predicting a colorectal cancer patient's risk of cancer recurrence or non-recurrence.

The invention provides systems, tools, kits, nucleic acid arrays, matrices, software, computer programs, and the like, adapted to utilize the prognostic biomarker genes (BMI1, ETV6, H3F3B, RPS10, and VEGFA) and/or prognostic rule(s) of the invention for predicting a subject's risk of colorectal cancer recurrence and/or non-recurrence. For example, a system, assay, kit, or surface may comprise one or more of the disclosed biomarker genes, amplification probes, hybridization probes, assay reagents, data collection, computation, and output modules, computer software, machine-readable media, and the like, adapted and/or designed to apply to a subject's determined level of gene expression to the prognostic rule(s) and generate an assessment of the risk of colorectal cancer recurrence and/or non-recurrence.

The invention further provides a method for predicting the risk of colorectal cancer recurrence and/or non-recurrence comprising determining an amount of gene expression of the prognostic biomarker genes (BMI1, ETV6, H3F3B, RPS10, and VEGFA) in a sample obtained from a patient, and applying the determined amount of expression of the biomarker genes to a prognostic rule for determining such risk. The prognostic rule may be a rule identified in the Examples below, or may be generated by supervised learning analysis of the expression of biomarker genes BMI, ETV6, H3F3B, RPS10, and VEGFA in a population of colorectal patient samples classified as demonstrating recurrence or non-recurrence. A preferred rule for predicting risk of recurrence or non-recurrence is Rule 1 shown below:

If $[(((BMI1/H3F3B)*VEGFA)-((ETV6/RPS10)*H3F3B)) \geq -4.4777]$ then recurrence.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Definitions

Figure 1:
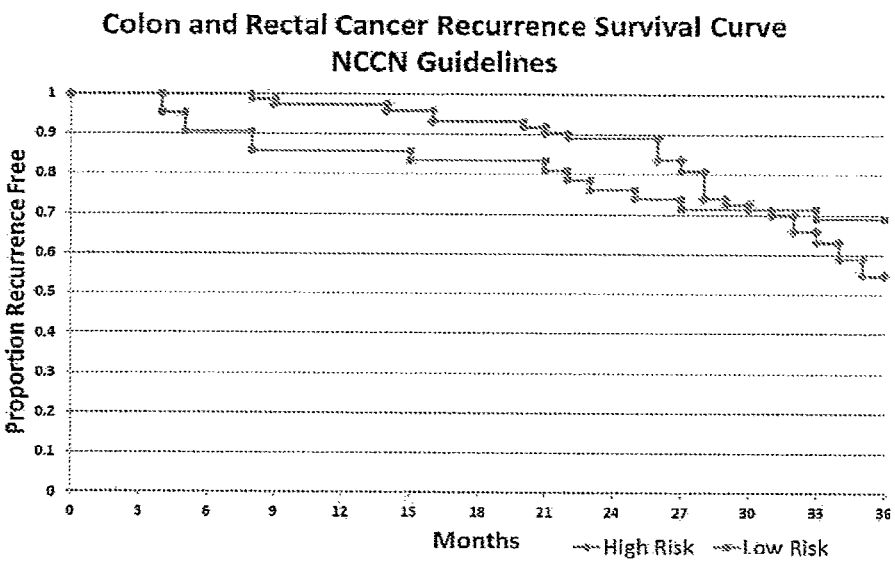
FIG. 1 is a graph showing the proportion of recurrence-free patients over a 3 year period for patient samples predicted in Example 2 to have high or low risk of recurrence of colorectal cancer according to prognostic Rule 1.
Figure 2:
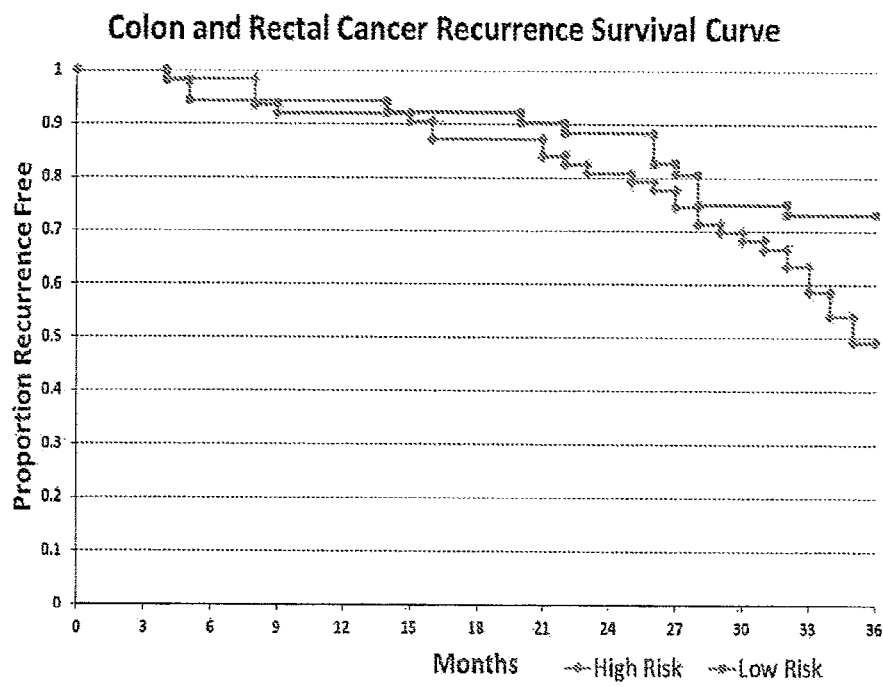
FIG. 2 is a graph showing survival curves for the same patient samples shown above in FIG. 1, but using NCCN Guidelines for predicting high or low risk of recurrence of colorectal cancer.

Unless otherwise noted, the present invention employs conventional techniques of molecular biology and related fields. Such techniques are described in the literature, including, for example, textbooks such as Sambrook et al., 2001, Molecular Cloning: A Laboratory Manual and Ausubel, et al., 2002, Short Protocols in Molecular Biology, (2002). All patents, patent applications, and publications mentioned herein are hereby expressly incorporated by reference in their entireties.

Unless defined otherwise, all technical and scientific terms used herein have the same meaning as commonly understood by those in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., at least one) of the grammatical object of the article. By way of example, "an element" means one or more element.

The term "patient sample" as used herein refers to a sample that may be obtained from a patient or subject and assayed for biomarker gene expression. The patient sample may include a biological fluid, tissue biopsy, and the like. In a preferred embodiment, the sample is a tissue sample, for example, tumor tissue, and may be fresh, frozen, and/or archival paraffin embedded tissue.

The term "gene" as used herein refers to any and all discrete coding regions of the cell's genome, as well as associated non-coding and regulatory regions. The gene is also intended to mean the open reading frame encoding specific polypeptides, introns, and adjacent 5' and 3' non-coding nucleotide sequences involved in the regulation of expression. In this regard, the gene may further comprise control signals such as promoters, enhancers, termination, and/or polyadenylation signals that are naturally associated with a given gene, or heterologous control signals. The DNA sequences may be cDNA or genomic DNA or a fragment thereof.

A "prognostic gene profile" refers to a combination of nucleic acid sequences whose quantitative expression levels can be used in a prognostic rule to predict the risk of cancer recurrence and/or non-recurrence in a patient. The prognostic gene profile identified herein comprises a combination of the following biomarker genes identified in the Examples below: BMI1, ETV6, H3F3B, RPS10, and VEGFA.

A "prognostic biomarker gene" of the present invention refers to the genes: BMI1, ETV6, H3F3B, RPS10, VEGFA, AKT1, ARAF, ARHGDIB, B2M, CD82, DIABLO, FGFR4, GUSB, HMOX1, ITGB1, MAPK14, MAX, MMP2, NFKB1, POLR2L, PSMB6, PTK2, and UBC.

A "prognostic rule" refers to a set of one or more mathematical expressions or algorithms relating the quantitative expression of the prognostic biomarker genes in a sample obtained from a colorectal cancer patient to a risk of cancer recurrence and/or non-recurrence.

"Supervised learning" as applied to the generation of a prognostic rule from the prognostic biomarker genes of Table 1, refers to a variety of mathematical learning techniques applied to a set of data where an outcome is defined, for example, recurrence or non-recurrence, and the analysis learns from the examples provided. Supervised learning techniques include, for example, Genetic Programming, CART analysis, Support Vector Machine, and Linear Discriminant Analysis, and the like.

"Recurrence" refers to the return of colorectal cancer to a patient within 36 months of treatment.

"Non-recurrence" refers to the confirmed absence of colorectal cancer in a patient for at least 36 months following treatment.

A "nucleic acid microarray" refers to an ordered arrangement of hybridizable nucleic acid array elements, such as polynucleotide probes, generally positioned on a substrate and capable of binding samples of complementary sequences through non-covalent binding interactions.

A peptide "fragment" or "portion" refers to a peptide comprising at least 10, 20, 30, 40, 50, 60, 70, 80, 90, 100, 125, 150, 175, 200, or 250 contiguous amino acid residues of the sequence of another peptide.

A gene or polynucleotide "fragment" or "portion" refers to a nucleic acid molecule comprising at least 10, 20, 30, 40, 50, 60, 70, 80, 90, 100, 125, 150, 175, 200, or 250 contiguous nucleic acid residues of the sequence of another polynucleotide.

The term "complement" used in reference to a nucleic acid sequence refers to a polynucleotide whose sequence is complementary to that of a second nucleic acid sequence and therefore able to hybridize to the second sequence.

A "probe" is an oligonucleotide or analog thereof that recognizes and able to hybridize to a polynucleotide target sequence through noncovalent (e.g., hydrogen bonding) interactions. The probe is generally of at least 8 nucleotides in length but is less than the full length of the gene. Probes may be modified with a detectable tag and/or a quencher molecule.

The term "isolated" and/or "purified" refers to a material that is separated from the components that normally accompany it in its native state. For example, an "isolated polynucleotide", as used herein, refers to a polynucleotide that has been purified from the sequences that flank the polynucleotide in a naturally-occurring state, such as a DNA fragment that has been removed from the sequences that are normally adjacent to the fragment.

The phrase "hybridizing specifically to" and the like refers to the binding, duplexing, or hybridizing of a molecule only to a particular nucleotide sequence under stringent conditions when that sequence is present in a complex mixture, for example, total cellular DNA or RNA, or a mixed polynucleotide extract thereof.

Identification of Biomarkers

As described in the Examples below, specific prognostic biomarker genes were identified by genetic programming analysis as exhibiting significant differential expression, either alone or in combination with other genes, between samples obtained from patients exhibiting cancer recurrence and patients that did not exhibit recurrence. In particular, the expression levels of the following five biomarker genes were identified as particularly useful in predicting risk of colorectal cancer recurrence: BMI1, ETV6, H3F3B, RPS10, and VEGFA.

The expression levels of these five significant biomarker genes may be subjected to further analyses as described in the Examples below to generate prognostic rules applying quantitative expression of a combination of these genes (prognostic genetic profile) to a prediction of colorectal cancer recurrence and/or non-recurrence. A prognostic gene profile useful for predicting colorectal cancer recurrence comprises a combination of the biomarker genes identified in the Examples below: BMI1, ETV6, H3F3B, RPS10, and VEGFA.

From the identified prognostic biomarker genes, prognostic rules can be generated using a variety of pattern recognition techniques and correlation analyses, such as genetic programming, linear regression, logistic regression, artificial neural networks, support vector machines (SVM), clustering models, CART analysis, and the like. In a preferred embodiment, genetic programming analysis of the biomarker genes is used to generate prognostic rules. The resultant prognostic rules are mathematical expressions (algorithms) relating the quantitative expression of prognostic biomarker genes to a risk of colorectal cancer recurrence and/or non-recurrence. An exemplary prognostic rule developed using Genetic Programming as described in the Examples below is the following preferred rule:

If [(((BMI1/H3F3B)*VEGFA)−((ETV6/RPS10) *H3F3B))≥−4.4777] then recurrence.

The expression of "housekeeping genes" can be used as a control in the analysis. Such housekeeping genes include, for example, GAPDH, beta-Actin, S9 ribosomal, ubiquitin, alpha-Tubulin, 18S rRNA, GUS, HPRT, B2M, TBP, CYC, HuPO, PGK, HuTfR, G6PDH (Blanquicett, et al., 2002, *Anal Biochem*, 303: 209-14); RPLP0, GAPD, HPRT1, B2M, POLR2A, RPS14, MAN1B1, ACTB, MTR (Dydensborg et al., 2006, *Am J Physiol Gastrointest Liver Physiol*, 290: G1067-74); and HPRT, ADA, TAF2, POLR2L, CETN2, ACTB, UBE2D2, PSMB6, CAPN2, TXNRD1, SDHA, GUS, CYCC, PMM1, AGPAT1, HDAC10, B2M (Rubie et al., 2005, *Mol Cell Probes*, 19:101-9).

Gene Expression Analysis

Gene expression can be quantitatively analyzed by a variety of known methods, for example, by determining an amount of mRNA, cDNA, or protein generated by gene expression in a sample, for example, a tissue sample. Methods for isolating mRNA from a tissue sample for further analysis are known, for example, see Ausubel et al., 2002, *Short Protocols in Molecular Biology*. Methods for isolating mRNA from paraffin embedded tissues are discussed, for example, in De Andres et al., 1995, *BioTechniques* 18:42044. RNA isolation kits are commercially available, including, for example, Paraffin Block RNA Isolations Kits (Ambion, Inc., Austin, Tex.).

Isolated RNA can be converted to cDNA and/or amplified, identified, and quantified by sequencing or by hybridization analysis, for example. Other methods for determining an amount of gene expression include, for example, northern blotting (Brown, 2001 May, *Curr Protoc Immunol.*, Chapter 10: Unit 10.12; Parker & Barnes, 1999, *Methods in Molecular Biology* 106:247-283), reverse transcriptase polymerase chain reaction (RT-PCR) (Nygaard et al. 2009, *Front Biosci.* 14:552-69; Weis et al., 1992, *Trends in Genetics* 8:263-64), RNAse protection assays (Emery, 1999, *Methods Mol Biol.* 362:343-8; Hod, 1992 *Biotechniques* 13:852-54), massively parallel signature sequencing (MPSS) (Kutlu, 2009, *BMC Med Genomics.*, 2:3; Brenner, 2000, *Nature Biotechnol.* 18:1021), Serial Analysis of Gene Expression (SAGE) (Boon 2009, *PLoS ONE.* 4:e5134; Velculescu, 1995, *Science* 270: 368-9, 371), and the use of antibodies capable of binding to DNA or RNA duplexes, RNA-mediated annealing, selection, and ligation (RASL) assay (Yeakley, 2002, *Nat Biotechnol;* 20:353-8), cDNA mediated annealing, selection, extension, and ligation (DASL) assay (Abramovitz, 2008, *Biotechniques*, 44:417-423; Fan, 2004, *Genome Research* 14:878-85), microarray techniques (Ravo et al., 2008, *Lab Invest*, 88:430-40; Schena, 1996, *Proc. Natl. Acad. Sci. USA*, 93:106-149), for example, Incyte's microarray technology or Affymetrix's GenChip technology; or high throughput sequencing techniques developed by 454 Life Sciences, Inc. (Branford, Conn.) (Marguilies, 2005, *Nature*, 437:376-80).

In one embodiment, the quantitative expression of the selected biomarker genes can be analyzed using commercial reagents, such as those available from APPLIED BIOSYSTEMS, including specific TAQMAN® Gene Expression Assays available for each of the five biomarkers of Rule 1. Exemplary TAQMAN® Gene Expression Assays are listed below. These were used in Example 2, described below.

TABLE 1

| SEQ ID | Biomarker | Assay Number | Amplicon length |
| --- | --- | --- | --- |
| 1 | BMI1 | Hs00180411_m1 | 105 nucleotides |
| 2 | ETV6 | Hs01045742_m1 | 75 nucleotides |
| 3 | H3F3B | Hs00855159_g1 | 83 nucleotides |
| 4 | RPS10 | Hs01652367_gH | 108 nucleotides |
| 5 | VEGFA | Hs00900055_m1 | 59 nucleotides |

DASL

The DASL assay method for determining quantitative gene expression includes conversion of total RNA to cDNA using biotinylated primers. The biotinylated DNA is attached to a streptavidin solid support, followed by annealing of assay oligonucleotides to their target sequences in the cDNA. A pair of oligonucleotides is annealed to a given target site, generally with three to ten target sites per gene. The upstream annealed oligonucleotides are extended and ligated to corresponding nucleotides downstream to create a PCR template that is amplified, for example, with universal PCR primers. The PCR products, labeled, for example, by incorporation of a labeled primer, are hybridized to capture sequences on a solid support array, and the fluorescence intensity is measured for each bead.

Complete custom designed DASL assay panels for up to 1536 genes comprising 1-3 probe groups per gene are available commercially from Illumina, Inc. (San Diego, Calif.), as well as a standard DASL human cancer panel comprising a set of probe groups targeting 502 genes that have been associated with cancer.

MassARRAY

The MassARRAY system is used to isolate and reverse transcribe RNA to cDNA. The cDNA is amplified, dephosphorylated, extended with primers, and placed onto a chip array for quantitative analysis via MALDI-TOF mass spectrometry. Hardware and software for carrying out MassARRAY analysis is commercially available from Sequenom, Inc. (San Diego, Calif.).

SAGE

In SAGE, multiple sequence tags of about 10-14 base pairs, each corresponding to a unique position within an RNA transcript are linked together to form extended molecules for sequencing, identifying the sequence of multiple tags simultaneously. A transcript's expression pattern can be quantified by determining the abundance of a given tag, and identifying the gene corresponding to that tag. Kits for performing SAGE as well as software for analyzing SAGE data are commercially available, including, for example, the I-SAGE Kit (Invitrogen, Carlsbad, Calif.). SAGE data can be used to search, for example, the SAGEmap database available via the Internet.

Genetic Programming

In a preferred embodiment, genetic programming is used to analyze gene expression data in order to identify a group of biomarker genes having sufficient predictive power for use in prognostic genetic profiles and in prognostic rules indicative of a subject's risk of colorectal cancer recurrence and/or non-recurrence.

Genetic programming is an artificial intelligence/machine learning technique that uses the principles of biological evolution to develop computer algorithms able to accomplish a task defined by the user (see, for example, Banzhaf et al., 1998, *Genetic Programming: An Introduction: On the Automatic Evolution of Computer Programs and Its Applications*;

Koza, J. R., 1992, *Genetic Programming. On the Programming of Computers by Means of Natural Selection*, MIT Press).

Genetic programming optimizes a set of computer programs to perform a desired task by evolving them in an iterative manner, using a measure of each program's fitness to perform "natural selection" of the population of programs. In an embodiment, of the invention, the task was to generate one or more prognostic rules useful in predicting the recurrence of cancer in a patient, and the measure of fitness, or "fitness function," was the ability of a given computer program's ability to correctly classify a tumor tissue sample as belonging to a patient that will experience recurrence or non-recurrence.

Evolution of the population of computer programs can be accomplished in a variety of known methods. One common method uses a crossover strategy, where a node of one program is exchanged with a node from another program present in the population. Another method to evolve a computer program is by mutation, wherein a node belonging to the program, or information contained in the node, is replaced without affecting any other program in the population. These methods can be used singly or together as with other methods that involve the exchange of component pieces of programming elements between programs. After each round of evolution, each computer program in the population is subjected to testing using the fitness measure.

As described in the Examples below, a genetic programming system can be presented with gene expression data taken from known samples of both target disease and healthy tissues, and be used to evolve a predicate IF-THEN clause for the targeted disease class, such as recurrence/non-recurrence of colorectal cancer. In an embodiment, the predicate IF-THEN clause is a mathematical expression relating the quantity of expression of various genes in tumor tissue to the likelihood of cancer recurrence in a patient. The evolved rules are developed using a training set of samples with the number of correctly classified samples being the measure of fitness of the candidate rules.

The fitness measure may be varied so that more weight is given to rules producing fewer false positive errors, or by giving more credit to rules that produce fewer false "negative" errors. The fitness measure may also be varied for other reasons that are external to the genetic programming system itself, but that better reflect desired goals. For example, in an embodiment it may be desirable to produce rules that only incorporate genes coding for specified classes of proteins, such as proteins known to escape a selected tumor tissue and enter the body systemically through the bloodstream.

Once a prognostic rule has been developed, the rule is checked against a test set of samples to evaluate its ability to generalize to unknown samples. After each round of fitness assessment, the best performing programs were retained for further evolution in the next round. Various methods may be used to select a computer program population for the next iteration of evolution. In an embodiment, the two fittest programs are "mated" with each other, using, for example, crossover, and the offspring programs are added to the program population for the next round of evolution, replacing the least fittest programs according to the fitness assessment. Additional iterations of evolution and fitness testing can be continued until one or more prognostic rules of suitable utility are obtained according to pre-selected criteria, or until no further improvement in fitness is observed.

A notable advantage to genetic programming is its ability to harness multiple variables and operators to produce an algorithm possessing high predictive power, often by combining variables in unexpected ways. An additional advantage over other modeling techniques is that a prognostic rule can be generated spontaneously without any operator input that would require, for example, the winnowing down of selected genes on the basis of association with biological processes thought to be significant to the disease under study, as may be necessary when using, for example, a hierarchical cluster analysis.

As with any analytical method, the utility of genetic programming can be compromised if suboptimal conditions are present. For example, ideally a large data set is available for partitioning into large training and test sets. In many cases, however, the total amount of input data is small, meaning the genetic programming system may not learn the most general classification concepts that are potentially available. Similarly, a small test does not allow a very thorough assessment of the generality of the learned concept. In these cases, there are known methods to evaluate results obtained from genetic programming that are external to the genetic programming system itself. For example, n-fold cross validation can be used to cope with small data sets. Those of skill will be able to select from the full spectrum of known validation methods.

A variety of genetic programming techniques can be used to practice the present invention. For example, genetic programming can be carried out according to the techniques described in U.S. Pat. No. 6,327,582.

Other Analytic Methods

It will be recognized that once a set of prognostic biomarker genes having high predictive power has been identified, analytical methods other than genetic programming could be used to generate one or more prognostic rules relating relative expression levels of the prognostic biomarker genes to cancer recurrence and/or non-recurrence. For example, known regression and other pattern recognition techniques can be used to generate predictive rules. Supervised learning techniques such as, CART analysis, Support Vector Machine, and Linear or Non-Linear Discriminant Analysis, and the like, are useful to develop prognostic rules once the prognostic biomarker genes are known.

Prognostic Rules

Prognostic rules for predicting the likelihood of colorectal cancer recurrence and/or non-recurrence in a patient are identified in the Examples below and can also be generated by analysis of the identified prognostic biomarker genes. The prognostic rules are generally Boolean expressions relating the amount of biomarker gene expression to the risk of colorectal cancer recurrence and/or non-recurrence.

A patient's likelihood of colorectal cancer recurrence is predicted by applying the patient's determined levels of biomarker gene expression to a prognostic rule. In one example, a computerized system comprises an input module to receive the gene expression values; an analytical module for applying the gene expression values to the prognostic rule and calculating a risk prediction according to the rule; and an output module for conveying the resultant risk prediction of recurrence and/or non-recurrence calculated by the rule to the user, for example, by display, or other communication mechanism. In another example, two or more rules may be applied to the analytical module.

Tools, Kits, Systems, and Prognostic Gene Profiles

The invention provides the group of genes identified as important biomarkers for risk of recurrence and/or non-recurrence in colorectal cancer patients. These prognostic biomarker genes are listed in Table 1, above. Prognostic genetic profiles and prognostic rules derived by mathematical analysis of the quantitative expression of these prognostic biomarker genes in exemplary patient samples are applied to assay methods, systems, tools, reagents, software, devices, and the like, for determining from an individual patient's level of expression of these prognostic biomarker genes a prediction of a probability of that patient belonging to a population that has a high risk of recurrence and/or non-recurrence of colorectal cancer, and to rational treatment of colorectal cancer patients based on the predicted prognosis.

Representative tools include, for example, assay systems adapted for determining an amount of expression of the prognostic biomarker genes, genetic profiles, and genes of specific prognostic rules, such as microarray, hybridization, amplification, PCR, DASL, SAGE, and similar assay systems, as well as kits, chips, cards, multi-well assay plates, probes, primers, data storage systems, software programs, computer systems, and the like that are used in a device, system, or method for predicting recurrence or non-recurrence of colorectal cancer in a patient.

Panels of nucleic acid probes and/or primers are designed to amplify and detect the expression levels of one or more of the prognostic biomarker genes. Such probes include, for example, isolated genes mRNA, cDNA, and portions thereof, amplified nucleic acids that are useful for the quantitative determination of gene expression levels. Such primers include nucleic acids flanking a desired amplicon and useful to amplify a desired gene or portion of a gene for quantifying gene expression.

An assay substrate such as a hybridization plate, chip, or card is adapted and designed to include primer pairs and/or probes that amplify and/or identify and/or sequence and thereby quantify the expression of the identified biomarker genes in a sample obtained from a subject.

Kits include reagents and tools useful in quantifying the expression levels of the identified biomarker genes that are associated with colorectal cancer recurrence due to their presence in prognostic rules of the invention and include, for example, nucleic acid probes and/or primers designed to quantify expression of the biomarker genes listed in Table 1.

Tools, kits, and systems also include computer systems, software, and modules adapted to store and apply the prognostic rules to calculate a predicted risk of colorectal cancer recurrence and/or non-recurrence. The computer system can include, for example, an input module for receiving quantitative biomarker gene expression data, an analytical module applying the prognostic rule and biomarker gene expression levels to calculate the mathematical outcome of the rule, and an output module for providing the predictive risk outcome.

Methods of Treatment or Prophylaxis

The present invention includes methods for predicting risk of colorectal cancer recurrence and/or non-recurrence in a patient. Generally, the method includes quantitatively determining from a patient's sample, the levels of expression for the genes of the identified prognostic gene profile listed in Table 1, applying the determined expression values to a prognostic rule, and interpreting the gene expression levels in accordance with the prognostic rule to determine the patient's risk of colorectal cancer recurrence. Treatment regimen is personalized to the patient's prognosis, as identified by the outcome of the application of the patient's gene expression data to the prognostic rule. In one example, a more aggressive anti-cancer regimen is applied where the analysis of the patient's sample indicates a likelihood of recurrence.

EXAMPLES

The invention may be readily understood and practiced with reference to the specific embodiments described in the following non-limiting examples. In the following examples, various assays are described as being utilized to select a set of expressed predictive genes. In particular, cDNA-mediated, Annealing, Selection, Extension, and Ligation (DASL) assay and Reverse Transcriptase Polymerase Chain Reaction (RT-PCR) Assay are described. However, the various embodiments of the invention are not limited to DASL and RT-PCR, but rather, may include any suitable genomic material selection assay.

Example 1

Generation of Gene Expression Profile of Stage I/II Colorectal Primary Adenocarcinoma Tissue Using the DASL Method Archival formalin-fixed, paraffin-embedded (FFPE) primary adenocarcinoma tissue was obtained during curative surgery from 145 patients having stage I or stage II colorectal cancer (104 colon, 41 rectal). All patients had either recurrence (R) by 36 months (mo) (n=67; 51 stage II) or confirmed non-recurrence (NR) for ≥36 mo (n=78; 56 stage II) post-op; none had neoadjuvant or adjuvant therapy. Patients were stratified by R status, time-to-first recurrence, right vs left-sided tumors, and/or the like and then randomly assigned to a Training Set (TSet) (n=73; 34R, 39NR) or Validation Set (VSet) (n=72; 33R, 39NR).

Training set tumor gene expression was quantified by a DASL assay (Illumina, San Diego, Calif.) (Abramovitz, 2008, *Biotechniques*, 44:417-423; Fan et al., 2004, *Genome Research* 14:878-85) using a custom 512 gene panel. Genes of interest exhibiting differential expression levels between the R and NR groups were identified and are shown in Table 2 together with a reference sequence position on the human genome, as listed in the U.C.S.C. genome browser available via the Internet and a representative nucleic acid sequence obtained from GenBank available via the Internet. The sequences in the U.C.S.C. Browser and GenBank as identified are hereby incorporated by reference.

Generation of Gene Expression Profile of Stage VII Colorectal Primary Adenocarcinoma Tissue Using the RT-PCR Method.

Alternatively or in addition to the DASL method, the gene expression profile may be generated using the RT-PCR method. For example, seventy-four (74) archival, clinically annotated, formalin-fixed paraffin-embedded (FFPE) primary carcinoma tissues obtained at initial surgical resection with curative intent (RO) were retrieved for 60 colon cancer (AJCC pT1-4 pN0 cM0) and 14 rectal cancer (AJCC pT2-3 pN0 cM0) patients from 1 US (Rochester, Minn.; n=45) and 2 separate European (Moscow, Russian Federation) sites. None had received neoadjuvant or adjuvant therapy. Thirty-six (36)-month R and NR status were confirmed for each case by medical records reviewed by site personnel. Informed consent was obtained for all patients.

After stratification by recurrence status, time-to-first recurrence, colon versus rectal cancer, R-versus L-sided colon, and tissue source, the 74 cases were randomly divided into a Training Set (n=37; 16R, 21NR) and an equally sized Test Set (n=37; 16R, 21NR).

To construct a custom focussed microarray, the tumor gene expression was assessed by RT-PCR with custom 384-well TaqMan® Low Density Arrays (Applied Biosystems, Foster City, Calif.). A panel of 417 cancer-associated genes was pre-selected for the arrays based on their meeting one or more of the following criteria: (1) Associated with tumorigenesis, tumor progression or metastasis; (2) Encode for key regulatory proteins in cell cycle progression, angiogenesis, survival, or apoptosis; (3) Involved in the initiation and progression of CRC; (4) Reported to be prognostic for CRC; (5) Predict or influence tumor response to CRC chemotherapies; (6) Differentially expressed between normal and malignant CRC tissue.

The appropriate mRNA reference sequence (REFSEQ) accession number was identified for each gene and the consensus sequence accessed through the NCBI Entrez nucleotide database. RT-PCR primers and probes were designed by Applied Biosystems. Amplicon sizes were kept to a minimum, with most being less than 100 bases in length.

For each case, after verification and localization of FFPE malignant tissue on an H&E stained slide by an independent gastrointestinal pathologist, corresponding unstained tumor tissue affixed to separate glass slides was scraped into RNAse-free microfuge tubes using a disposable scalpel. The tissue was de-paraffinized in xylene and RNA extracted and purified using the RecoverAll™ Total Nucleic Acid Isolation Kit (Applied Biosystems/Ambion, Austin, Tex.). Purity and quantity of RNA solutions were determined by measuring UV absorption ratios of 260/280 nm using the Nanodrop 1000 UV/Vis spectrophotometer. A minimum of 100 ng RNA was transcribed into single stranded cDNA using the High Capacity cDNA Reverse Transcription Kit (Applied Biosystems), employing random hexamers as primers. cDNA was either used immediately for RT-PCR or stored at −80° C.

Gene expression via real-time PCR was assayed using TaqMan® custom array 384-well microfluidic cards (Applied Biosytems). After 100 µl of cDNA (1 ng/µl) per 48 wells was applied to the cards, all assays were performed in duplicate using the 7900HT Fast Real-Time PCR System. Output data was in number of PCR cycles needed to reach a constant threshold set at 0.2 on the amplification curve, i.e., cycle threshold (Ct). The data was normalized using 5 housekeeping (HK) genes to correct for potential technical variability and deviation in RNA integrity and quantity in each assay. The 5 HK genes selected (B2M, GUSB, POLR2L, PSMB6, UBC) showed the lowest levels of expression variability out of 9 candidate genes well-known to be constitutively expressed in CRC and other tissues. Each pair of individual gene expression replicates was inspected for congruence and a correlation coefficient was generated for each. The replicates were averaged and the resulting data normalized by subtracting the Ct for each rule gene (RG Ct) from the average of the 5 HK genes (Ave. 5HK Ct). Since Ct values are expressed as logarithmic numbers to the base 2, the data was linearized by taking the antilog and the result was scaled by a factor of 100. Thus the final form of the data was:

$$\text{Gene expression value} = 2^{(Ave.\ 5HK\ Ct-RG\ Ct)} \times 100.$$

Throughout the study, the following were the minimal criteria for acceptance of extracted RNA and RT-PCR results: (1) RNA concentration: ≥10 ng/µl; (2) RNA was required to have a 260/280 nm ratio of ≥1.8; (3) average expression of the 5 HK genes: ≤32.0 Ct; and (4) all individual Ct values: ≤35.

TABLE 2

| Name | GenBank No: | Human Genome Position |
| --- | --- | --- |
| BMI1 | Ref seq NM_005180.8 | Chr10: 22,605,299-22,620,417 |
| ETV6 | Ref seq NM_001987.4 | Chr12: 11,802,788-12,048,323 |
| H3F3B | Ref seq NM_005324.3 | Chr1: 226,250,421-226,259,702 |
| RPS10 | mRNA BE397113.1 | Chr6: 34,385,233-34,393,876 |
| VEGFA | Ref sequences: | Chr6: 43,737,953-43,754,221 |
|  | NM_0010256366.2 |  |
|  | NM_001025367.2 |  |
|  | NM_001025368.2 |  |

TABLE 2-continued

| Name | GenBank No: | Human Genome Position |
| --- | --- | --- |
|  | NM_001025369.2 |  |
|  | NM_001025370.2 |  |
|  | NM_001033756.2 |  |
|  | NM_001171630.1 |  |
|  | NM_001171629.1 |  |
|  | NM_001171628.1 |  |
|  | NM_001171627.1 |  |
|  | NM_001171626.1 |  |
|  | NM_001171625.1 |  |
|  | NM_001171624.1 |  |
|  | NM_001171623.1 |  |
|  | NM_001171622.1 |  |
|  | NM_003376.5 |  |

Example 2

Generation of Rules for Determining Risk of Recurrence of Colorectal Cancer Via Genetic Programming The prognostic biomarker genes identified in Example 1 were analyzed using successive genetic programming (GP) analyses of the training set gene expression data to evolve prognostic rules, based on expression levels of biomarker genes. These rules, shown below, were useful in predicting in a validation data set whether a colorectal cancer patient would experience recurrence or non-recurrence.

In the genetic programming analysis of the identified prognostic biomarker genes, a population of potential rules including various combinations of the genes of Table 2 was randomly generated to produce a set of candidate rules. Each candidate rule was then tested for fitness.

The number of tumor tissue samples correctly classified as "recurrence" versus "non-recurrence" served as the measure of fitness for the candidate rule. In another example, the sum of the sensitivity and specificity, or the sum of the positive predictability, negative predictability, and the like, are utilized as the measure of fitness. In another example, the area under the curve (AUC) of the receiver operator curve (ROC) is used as the measure of fitness. If candidate rules judged as having a sufficiently high fitness were found, the genetic programming was terminated, and the fittest candidates were selected as prognostic rules. If the termination criterion was not met, candidate rules having the highest fitness were mated to produce a new population of offspring candidate rules, and the candidate rules found to have lower fitness were discarded.

Additional iterations of the genetic programming method were performed until the termination criterion was satisfied and one or more rules of suitable fitness were discovered. After successive GP analyses of the genes of Table 2, the input data resulted in a prognostic signature rule that predicted recurrence (see Table 3).

TABLE 3

| Rule | GP RULE for CRC RECURRENCE |
| --- | --- |
| 1 | IF [(((BMI1/H3F3B) * VEGFA) − ((ETV6/RPS10) * H3F3B)) ≥ −4.4777] THEN RECURRENCE |

Example 3

Use of the Prognostic GP Rule to Predict Recurrence

The rule of Table 3 was used to predict recurrence in colorectal cancer patients. Archival formalin-fixed paraffin-embedded primary adenocarcinoma tissues (median storage 7 years; range 4-15) obtained at initial surgical resection with curative intent was retrieved for 86 stage I/II (pT1-4 pN0 M0) colon cancer patients and 29 stage I (pT1-2, pN0 M0) rectal cancer patients from 2 sites in the United States and 2 European sites. These sites and samples were different from those samples that were used to generate the molecular test as described above for Examples 1 and 2.

The obtained samples included those from patients having tumor recurrence (R) within 36 months of surgery (n=46) and those from patients confirmed as non-recurrence (NR) for at least 36 months after surgery (n=69). None of the patients had received neoadjuvant or adjuvant therapy.

Tumor gene expression was assessed in these samples by qRT-PCR using custom 384-well TAQMAN® Low Density Arrays obtained from APPLIED BIOSYSTEMS and using RNA that had satisfied a set of rigorous quality control parameters. The TAQMAN® Assay Number and probe length for each of the 5 queried genes are shown in Table 4 below:

TABLE 4

| Biomarker Gene | TAQMAN probe length | TAQMAN Assay Number |
| --- | --- | --- |
| BMI1 | 105 nt | Hs00180411_m1 |
| ETV6 | 75 nt | Hs01045742_m1 |
| H3F3B | 83 nt | Hs00855159_g1 |
| RPS10 | 108 nt | Hs01652367_gH |
| VEGFA | 59 nt | Hs00900055_m1 |

The predictive sensitivity and specificity of Rule 1 were analyzed in this set of patient data (VSet) and compared to that obtained using the current National Comprehensive Cancer Network (NCCN) for colorectal cancer. For stages I/II CRC (n=115), the dichotomous rule correctly classified 32/46 R and 38/69 NR VSet patients with 70% sensitivity and 55% specificity. Those patients deemed 'high risk' had a significantly higher probability of recurrence within 36 months than those labeled 'low risk', with a positive predictive value (PPV) of 51%, a negative predictive value (NPV) of 73%, and a relative hazard (HR) of 2.06 (95% CI: 1.1 to 3.86; p=0.020).

In contrast, the NCCN Guidelines (Version 1.2011) were not able to differentiate 36-month recurrence versus non-recurrence as well in this population, having a 72% sensitivity and 42% specificity, a positive predictive value of 45% and negative predictive value of 69%. The hazard ratio was 1.38 (95% CI: 0.73-2.53, p=0.315). The specificity of the molecular test was significantly greater than that for NCCN (p=0.05).

For stage I rectal cancer patients, (n=29; 13 recurrences), prognostic accuracy of the molecular test showed 79% specificity (23/29) surpassing the 55% specificity (16/29) of the NCCN guidelines (16/29).

In this example, a prognostic rule derived from prognostic biomarker genes identified as important to the determination of colorectal cancer recurrence and/or non-recurrence by genetic programming analysis of gene expression levels in FFPE tumor tissue, and was better able to differentiate early stage CRC patients at high versus low risk for recurrence within 3 years than the current NCCN Guidelines.

Example 4

Use of the Prognostic GP Rule to Predict Recurrence

As described above, Genetic Programming was used to identify prognostic biomarker genes (Example 1) and to generate prognostic rules for determining the risk of colorectal cancer recurrence (Examples 2 and 3). Since expression levels of the prognostic biomarker genes listed in Table 2 were highly predictive of colorectal cancer recurrence, we hypothesized that prognostic rules based upon expression of these prognostic biomarker genes could also be generated using non-GP analytic methods.

To demonstrate the usefulness of other methods of analyses, prognostic rules derived from expression of the prognostic biomarker genes listed in Table 2 can be generated using a Classification and Regression Tree (CART) algorithm (Freund et al. 1999, *The alternating decision tree learning algorithm*).

To further demonstrate use of the prognostic biomarker genes in prognostic rules generated by a variety of analytical techniques, a support vector machine can be created using the expression data and known recurrence and non-recurrence Tset data for the genes listed in Table 2. (See, for example, Mocellin et al. 2003 *Ann Surg Oncol.* 2006 13: 1113-1122). The support vector machine (SVM) created by the coefficients and vectors is used to perform a 4-fold crossvalidation on the training data (Tset) to test the robustness of the classifier. The classifier is trained on the 3 folds and the accuracy is tested on the fourth. The analysis is reported in single accuracies (%) and total accuracy (average over the four folds) (%). Testing of the validation set (Vset) with the rule developed by SVM produces a reported accuracy (%).

To further demonstrate use of the prognostic biomarker genes in prognostic rules generated by a variety of analytical techniques, a support vector machine can be created using the quantitative expression data and known recurrence and non-recurrence Tset data for the genes listed in Table 2. (See, for example, Mocellin et al. 2003 *Ann Surg Oncol.* 2006 13: 1113-1122). The support vector machine created by the coefficients and vectors is used to perform a 4-fold cross-validation on the training data (Tset) to test the robustness of the classifier. The classifier is trained on the 3 folds and the accuracy is tested on the fourth.

To further demonstrate the highly predictive power of the prognostic biomarker genes listed in Table 2, prognostic rules predicting the likelihood of recurrence of colorectal cancer based upon quantitative expression of the genes listed in Table 2 are generated using a linear discriminant analysis (see, for example, Marchevsky et al., 2004 *JMD, Vol.* 6: 1 Estévez et al., 2004, *Eur Clin Nutr* 58:449-455).

Linear discriminant (LD) analysis uses both the individual measurements of each gene and the calculated measurements of all combinations of genes to classify samples into two groups. For each gene a weight is derived from the mean and standard deviation of the Group 1 and Group 2 groups. Every gene is multiplied by a weight and the sum of these values results in a collective discriminate score. This discriminant score is then compared against collective centroids of the Group 1 and Group 2 groups. These centroids are the average of all Group 1 and Group 2 samples respectively. Therefore, each gene contributes to the overall prediction. This contribution is dependent on weights that are large positive or negative numbers if the relative distances between the Group 1 and Group 2 samples for that gene are large, and small numbers if the relative distances are small. The discriminant score for each unknown sample and centroid values can be used to calculate a probability between zero and one as to which group the unknown sample belongs.

In another embodiment of the invention, genes in addition to those listed in Table 1 are utilized to generate a gene expression profile.

Example 5

Generation of Gene Expression Profile of Stage I/II Colorectal Primary Adenocarcinoma Tissue Using the RT-PCR Method Seventy-four (74) archival, clinically annotated, formalin-fixed paraffin-embedded (FFPE) primary carcinoma tissues obtained at initial surgical resection with curative intent (R0) were retrieved for 60 colon cancer (AJCC pT1-4 pN0 cM0) and 14 rectal cancer (AJCC pT2-3 pN0 cM0) patients from 1 US (Rochester, Minn.; n=45) and 2 separate European (Moscow, Russian Federation) sites. None had received neoadjuvant or adjuvant therapy. Thirty-six (36)-month R and NR status were confirmed for each case by medical records reviewed by site personnel. Informed consent was obtained for all patients.

After stratification by recurrence status, time-to-first recurrence, colon versus rectal cancer, R-versus L-sided colon, and tissue source, the 74 cases were randomly divided into a Training Set (n=37; 16R, 21NR) and an equally sized Test Set (n=37; 16R, 21NR).

To construct a custom focused microarray, the tumor gene expression was assessed by RT-PCR with custom 384-well TaqMan® Low Density Arrays (Applied Biosystems, Foster City, Calif.). A panel of 417 cancer-associated genes was pre-selected for the arrays based on their meeting one or more of the following criteria: (1) Associated with tumorigenesis, tumor progression or metastasis; (2) Encode for key regulatory proteins in cell cycle progression, angiogenesis, survival, or apoptosis; (3) Involved in the initiation and progression of CRC; (4) Reported to be prognostic for CRC; (5) Predict or influence tumor response to CRC chemotherapies; (6) Differentially expressed between normal and malignant CRC tissue.

The appropriate mRNA reference sequence (REFSEQ) accession number was identified for each gene and the consensus sequence accessed through the NCBI Entrez nucleotide database. RT-PCR primers and probes were designed by Applied Biosystems. Amplicon sizes were kept to a minimum, with most being less than 100 bases in length.

For each case, after verification and localization of FFPE malignant tissue on an H&E stained slide by an independent gastrointestinal pathologist, corresponding unstained tumor tissue affixed to separate glass slides was scraped into RNAse-free microfuge tubes using a disposable scalpel. The tissue was de-paraffinized in xylene and RNA extracted and purified using the RecoverAll™ Total Nucleic Acid Isolation Kit (Applied Biosystems/Ambion, Austin, Tex.). Purity and quantity of RNA solutions were determined by measuring UV absorption ratios of 260/280 nm using the Nanodrop 1000 UV/Vis spectrophotometer. A minimum of 100 ng RNA was transcribed into single stranded cDNA using the High Capacity cDNA Reverse Transcription Kit (Applied Biosystems), employing random hexamers as primers. cDNA was either used immediately for RT-PCR or stored at −80° C.

Gene expression via real-time PCR was assayed using TaqMan® custom array 384-well microfluidic cards (Applied Biosytems). After 100 µl of cDNA (1 ng/µl) per 48 wells was applied to the cards, all assays were performed in duplicate using the 7900HT Fast Real-Time PCR System. Output data was in number of PCR cycles needed to reach a constant threshold set at 0.2 on the amplification curve, i.e., cycle threshold (Ct). The data was normalized using 5 housekeeping (HK) genes to correct for potential technical variability and deviation in RNA integrity and quantity in each assay. The 5 HK genes selected (B2M, GUSB, POLR2L, PSMB6, UBC) showed the lowest levels of expression variability out of 9 candidate genes well-known to be constitutively expressed in CRC and other tissues. Each pair of individual gene expression replicates was inspected for congruence and a correlation coefficient was generated for each. The replicates were averaged and the resulting data normalized by subtracting the Ct for each rule gene (RG Ct) from the average of the 5 HK genes (Ave. 5HK Ct). Since Ct values are expressed as logarithmic numbers to the base 2, the data was linearized by taking the antilog and the result was scaled by a factor of 100. Thus the final form of the data was:

$$\text{Gene expression value} = 2^{(Ave.\ 5HK\ Ct - RG\ Ct)} \times 100.$$

Throughout the study, the following were the minimal criteria for acceptance of extracted RNA and RT-PCR results: (1) RNA concentration: ≥10 ng/µl; (2) RNA was required to have a 260/280 nm ratio of ≥1.8; (3) average expression of the 5 HK genes: ≤32.0 Ct; and (4) all individual Ct values: ≤35.

Genes of interest exhibiting differential expression levels between the R and NR groups were identified by the RT-PCR assay described herein and are shown in Table 5 together with a reference sequence position on the human genome, as listed in the U.C.S.C. genome browser available via the Internet and a representative nucleic acid sequence obtained from GenBank available via the Internet. The sequences in the U.C.S.C. Browser and GenBank as identified are hereby incorporated by reference.

TABLE 5

| SEQ ID | Name | GenBank No: | Human Genome Position |
|---|---|---|---|
| 1 | BMI1 | Ref seq NM_005180.8 | chr10: 22,605,299-22,620,417 |
| 2 | ETV6 | Ref seq NM_001987.4 | Chr12: 11,802,788-12,048,323 |
| 3 | H3F3B | Ref seq NM_005324.3 | chr1: 226,250,421-226,259,702 |
| 4 | RPS10 | mRNA BE397113.1 | chr6: 34,385,233-34,393,876 |
| 5 | VEGFA | Ref sequences: NM_0010256366.2 NM_001025367.2 NM_001025368.2 NM_001025369.2 NM_001025370.2 NM_001033756.2 NM_001171630.1 NM_001171629.1 NM_001171628.1 NM_001171627.1 NM_001171626.1 NM_001171625.1 NM_001171624.1 NM_001171623.1 NM_001171622.1 NM_003376.5 | chr6: 43,737,953-43,754,221 |
| 6 | AKT1 | BC000479.2 | |
| 7 | ARAF | BC007514.2 | |
| 8 | ARHGDIB | NM_001175.4 | |
| 9 | B2M | NM_004048.2 | |
| 10 | CD82 | BC000726.2 | |
| 11 | DIABLO | NM_019887.4 | |
| 12 | FGFR4 | L03840.1 | |
| 13 | GUSB | NM_000181.3 | |
| 14 | HMOX1 | NM_002133.2 | |
| 15 | ITGB1 | NM_002211.3 | |
| 16 | MAPK14 | BC031574.1 | |

TABLE 5-continued

| SEQ ID | Name | GenBank No: | Human Genome Position |
|---|---|---|---|
| 17 | MAX | BC036092.1 | |
| 18 | MMP2 | BC002576.2 | |
| 19 | NFKB1 | NM_003998.3 | |
| 20 | POLR2L | NM_021128.4 | |
| 21 | PSMB6 | NM_002798.1 | |
| 22 | PTK2 | BC035404.2 | |
| 23 | UBC | NM_021009.5 | |

Example 6

Generation of Rules for Determining Risk of Recurrence of Colorectal Cancer Via Genetic Programming The prognostic biomarker genes identified in Example 5 were analyzed using successive genetic programming (GP) analyses of the training set gene expression data to evolve prognostic rules, based on expression levels of biomarker genes. These rules, shown below, were useful in predicting in a validation data set whether a colorectal cancer patient would experience recurrence or non-recurrence.

In the genetic programming analysis of the identified prognostic biomarker genes, a population of potential rules including various combinations of the genes of Table 5 was randomly generated to produce a set of candidate rules. Each candidate rule was then tested for fitness.

The number of tumor tissue samples correctly classified as "recurrence" versus "non-recurrence" served as the measure of fitness for the candidate rule. If candidate rules judged as having a sufficiently high fitness were found, the genetic programming was terminated, and the fittest candidates were selected as prognostic rules. If the termination criterion was not met, candidate rules having the highest fitness were mated to produce a new population of offspring candidate rules, and the candidate rules found to have lower fitness were discarded.

Additional iterations of the genetic programming method were performed until the termination criterion was satisfied and one or more rules of suitable fitness were discovered. After successive GP analyses of the genes of Table 5, the input data resulted in the prognostic signature rules that predicted recurrence (see Table 6).

TABLE 6

| Rule | GP RULE for CRC RECURRENCE |
|---|---|
| 1 | IF [(((BMI1/H3F3B) × VEGFA)−((ETV6/RPS10) × H3F3B)) ≥ 4.4777] THEN RECURRENCE |
| 2 | IF [((AKT1 * BMI1) * (RPS10/MMP2))] >= 90.169556 THEN RECURRENCE |
| 3 | IF [((HMOX1/ARHGDIB) * (AKT1/H3F3B))] >= 0.087297 THEN RECURRENCE |
| 4 | IF [((AKT1/NFKB1) * (RPS10/CD82))] >= 7.500713 THEN RECURRENCE |
| 5 | IF [((AKT1/ETV6) * (RPS10/CD82))] >= 14.345780 THEN RECURRENCE |
| 6 | IF [(ARAF/(MMP2 * (ARHGDIB/HMOX1)))] >= 0.049082 THEN RECURRENCE |
| 7 | IF [((AKT1/H3F3B) * (BMI1/HMOX1))] >= 0.305097 THEN RECURRENCE |
| 8 | IF [((AKT1 * RPS10) * (HMOX1/MMP2))] >= 110.769318 THEN RECURRENCE |

Example 7

Use of the Prognostic GP Rule to Predict Recurrence

The rules of Table 6 were used to predict recurrence in colorectal cancer patients. Archival formalin-fixed paraffin-embedded primary adenocarcinoma tissues (median storage 7 years; range 4-15) obtained at initial surgical resection with curative intent was retrieved for 86 stage I/II (pT1-4 pN0 M0) colon cancer patients and 29 stage I (pT1-2, pN0 M0) rectal cancer patients from 2 sites in the United States and 2 European sites. These sites and samples were different from those samples that were used to generate the molecular test as described above for Examples 5 and 6.

The obtained samples included those from patients having tumor recurrence (R) within 36 months of surgery (n=46) and those from patients confirmed as non-recurrence (NR) for at least 36 months after surgery (n=69). None of the patients had received neoadjuvant or adjuvant therapy.

Tumor gene expression was assessed in these samples by qRT-PCR using custom 384-well TAQMAN® Low Density Arrays obtained from APPLIED BIOSYSTEMS and using RNA that had satisfied a set of rigorous quality control parameters. The TAQMAN® Assay Number and probe length for each of the 23 queried genes are shown in Table 7 below:

TABLE 7

| SEQ ID | Biomarker Gene | TAQMAN probe length | TAQMAN Assay Number |
|---|---|---|---|
| 1 | BMI1 | 105 nt | Hs00180411_m1 |
| 2 | ETV6 | 75 nt | Hs01045742_m1 |
| 3 | H3F3B | 83 nt | Hs00855159_g1 |
| 4 | RPS10 | 108 nt | Hs01652367_gH |
| 5 | VEGFA | 59 nt | Hs00900055_m1 |
| 6 | AKT1 | 66 nt | Hs00178289_m1 |
| 7 | ARAF | 74 nt | Hs00176427_m1 |
| 8 | ARHGDIB | 81 nt | Hs00171288_m1 |
| 9 | B2M | 64 nt | Hs00187842_m1 |
| 10 | CD82 | 86 nt | Hs00356310_m1 |
| 11 | DIABLO | 70 nt | Hs00219876_m1 |
| 12 | FGFR4 | 74 nt | Hs00242558_m1 |
| 13 | GUSB | 81 nt | Hs99999908_m1 |
| 14 | HMOX1 | 82 nt | Hs01110250_m1 |
| 15 | ITGB1 | 86 nt | Hs01127543_m1 |
| 16 | MAPK14 | 91 nt | Hs01051152_m1 |
| 17 | MAX | 61 nt | Hs00231142_m1 |
| 18 | MMP2 | 84 nt | Hs01548733_m1 |
| 19 | NFKB1 | 73 nt | Hs00231653_m1 |
| 20 | POLR2L | 74 nt | Hs00360764_m1 |
| 21 | PSMB6 | 93 nt | Hs00382586_m1 |
| 22 | PTK2 | 68 nt | Hs00178587_m1 |
| 23 | UBC | 71 nt | Hs00824723_m1 |

The predictive sensitivity and specificity of Rules 1 to 8 were analyzed in this set of patient data (Vset) and compared to that obtained using the current National Comprehensive Cancer Network (NCCN) Guidelines for colorectal cancer. For stages I/II CRC (n=115), the dichotomous rule correctly classified 32/46 R and 38/69 NR VSet patients with 70% sensitivity and 55% specificity. Those patients deemed 'high risk' had a significantly higher probability of recurrence within 36 months than those labeled 'low risk', with a positive predictive value (PPV) of 51%, a negative predictive value (NPV) of 73%, and a relative hazard (HR) of 2.06 (95% CI: 1.1 to 3.86; p=0.020).

In contrast, the NCCN Guidelines (Version 1.2011) were not able to differentiate 36-month recurrence versus non-recurrence in this population, 72% sensitivity and 42% specificity, a positive predictive value of 45% and negative predictive value of 69%. The hazard ratio was 1.38 (95% CI: 0.73-

2.53, p=0.315). The specificity of the molecular test was significantly greater than that for NCCN (p=0.05).

For stage I rectal cancer patients, (n=29; 13 recurrences), prognostic accuracy of the molecular test showed 79% specificity (23/29) surpassing the 55% specificity (16/29) of the NCCN guidelines In this example, a prognostic rule derived from prognostic biomarker genes identified as important to the determination of colorectal cancer recurrence and/or non-recurrence by genetic programming analysis of gene expression levels in FFPE tumor tissue, and was better able to differentiate early stage CRC patients at high versus low risk for recurrence within 3 years than the current NCCN Guidelines.

Example 8

Use of the Prognostic GP Rules to Predict Recurrence

As described above, Genetic Programming was used to identify prognostic biomarker genes (Example 5) and to generate prognostic rules for determining the risk of colorectal cancer recurrence (Examples 6 and 7). Since expression levels of the prognostic biomarker genes listed in Table 5 were highly predictive of colorectal cancer recurrence, we hypothesized that prognostic rules based upon expression of these prognostic biomarker genes could also be generated using non-GP analytic methods.

To demonstrate the usefulness of other methods of analyses, prognostic rules derived from expression of the prognostic biomarker genes listed in Table 5 can be generated using a Classification and Regression Tree (CART) algorithm (Freund et al. 1999, *The alternating decision tree learning algorithm*).

To further demonstrate use of the prognostic biomarker genes in prognostic rules generated by a variety of analytical techniques, a support vector machine can be created using the expression data and known recurrence and non-recurrence Tset data for the genes listed in Table 5. (See, for example, Mocellin et al. 2003 *Ann Surg Oncol.* 2006 13: 1113-1122). The support vector machine (SVM) created by the coefficients and vectors is used to perform a 4-fold crossvalidation on the training data (Tset) to test the robustness of the classifier. The classifier is trained on the 3 folds and the accuracy is tested on the fourth. The analysis is reported in single accuracies (%) and total accuracy (average over the four folds) (%). Testing of the validation set (Vset) with the rule developed by SVM produces a reported accuracy (%).

To further demonstrate use of the prognostic biomarker genes in prognostic rules generated by a variety of analytical techniques, a support vector machine can be created using the quantitative expression data and known recurrence and non-recurrence Tset data for the genes listed in Table 5. (See, for example, Mocellin et al. 2003 *Ann Surg Oncol.* 2006 13: 1113-1122). The support vector machine created by the coefficients and vectors is used to perform a 4-fold cross-validation on the training data (Tset) to test the robustness of the classifier. The classifier is trained on the 3 folds and the accuracy is tested on the fourth.

To further demonstrate the highly predictive power of the prognostic biomarker genes listed in Table 5, prognostic rules predicting the likelihood of recurrence of colorectal cancer based upon quantitative expression of the genes listed in Table 5 are generated using a linear discriminant analysis (see, for example, Marchevsky et al., 2004 *JMD, Vol.* 6: 1Estévez et al., 2004, *Eur Clin Nutr* 58:449-455).

Linear discriminant (LD) analysis uses both the individual measurements of each gene and the calculated measurements of all combinations of genes to classify samples into two groups. For each gene a weight is derived from the mean and standard deviation of the Group 1 and Group 2 groups. Every gene is multiplied by a weight and the sum of these values results in a collective discriminate score. This discriminant score is then compared against collective centroids of the Group 1 and Group 2 groups. These centroids are the average of all Group 1 and Group 2 samples respectively. Therefore, each gene contributes to the overall prediction. This contribution is dependent on weights that are large positive or negative numbers if the relative distances between the Group 1 and Group 2 samples for that gene are large, and small numbers if the relative distances are small. The discriminant score for each unknown sample and centroid values can be used to calculate a probability between zero and one as to which group the unknown sample belongs.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A kit or assay system for determining risk of colorectal cancer recurrence, the kit or assay system consisting of a set of cDNA molecules, wherein the set of cDNA molecules consists of:
   (i) a cDNA molecule consisting of the nucleotide sequence of SEQ ID NO: 1;
   (ii) a cDNA molecule consisting of the nucleotide sequence of SEQ ID NO: 2;
   (iii) a cDNA molecule consisting of the nucleotide sequence of SEQ ID NO: 3;
   (iv) a cDNA molecule consisting of the nucleotide sequence of SEQ ID NO: 4; and
   (v) a cDNA molecule consisting of the nucleotide sequence of SEQ ID NO: 5.

2. A microarray for quantitative analysis of expression of a prognostic colorectal cancer gene profile consisting of a set of cDNA molecules and optionally, a substrate on which the set of cDNA molecules is immobilized, wherein the set of cDNA molecules consists of:
   (i) a cDNA molecule consisting of the nucleotide sequence of SEQ ID NO: 1;
   (ii) a cDNA molecule consisting of the nucleotide sequence of SEQ ID NO: 2;
   (iii) a cDNA molecule consisting of the nucleotide sequence of SEQ ID NO: 3;
   (iv) a cDNA molecule consisting of the nucleotide sequence of SEQ ID NO: 4; and
   (v) a cDNA molecule consisting of the nucleotide sequence of SEQ ID NO: 5.

3. A kit or assay system for determining risk of colorectal cancer recurrence, the kit or assay system consisting of a set of cDNA molecules, wherein the set of cDNA molecules consists of:
   (i) a cDNA molecule consisting of the nucleotide sequence of SEQ ID NO: 1;
   (ii) a cDNA molecule consisting of the nucleotide sequence of SEQ ID NO: 2;
   (iii) a cDNA molecule consisting of the nucleotide sequence of SEQ ID NO: 3;
   (iv) a cDNA molecule consisting of the nucleotide sequence of SEQ ID NO: 4;
   (v) a cDNA molecule consisting of the nucleotide sequence of SEQ ID NO: 5;
   (vi) a cDNA molecule consisting of the nucleotide sequence of SEQ ID NO: 6;
   (vii) a cDNA molecule consisting of the nucleotide sequence of SEQ ID NO: 7;
   (viii) a cDNA molecule consisting of the nucleotide sequence of SEQ ID NO: 8;
   (ix) a cDNA molecule consisting of the nucleotide sequence of SEQ ID NO: 10;
   (x) a cDNA molecule consisting of the nucleotide sequence of SEQ ID NO: 14;
   (xi) a cDNA molecule consisting of the nucleotide sequence of SEQ ID NO: 18; and
   (xii) a cDNA molecule consisting of the nucleotide sequence of SEQ ID NO: 19.

4. A microarray for quantitative analysis of expression of a prognostic colorectal cancer gene profile consisting of a set of cDNA molecules and optionally, a substrate on which the set of cDNA molecules is immobilized, wherein the set of cDNA molecules consists of:
   (i) a cDNA molecule consisting of the nucleotide sequence of SEQ ID NO: 1;
   (ii) a cDNA molecule consisting of the nucleotide sequence of SEQ ID NO: 2;
   (iii) a cDNA molecule consisting of the nucleotide sequence of SEQ ID NO: 3;
   (iv) a cDNA molecule consisting of the nucleotide sequence of SEQ ID NO: 4;
   (v) a cDNA molecule consisting of the nucleotide sequence of SEQ ID NO: 5;
   (vi) a cDNA molecule consisting of the nucleotide sequence of SEQ ID NO: 6;
   (vii) a cDNA molecule consisting of the nucleotide sequence of SEQ ID NO: 7;
   (viii) a cDNA molecule consisting of the nucleotide sequence of SEQ ID NO: 8;
   (ix) a cDNA molecule consisting of the nucleotide sequence of SEQ ID NO: 10;
   (x) a cDNA molecule consisting of the nucleotide sequence of SEQ ID NO: 14;
   (xi) a cDNA molecule consisting of the nucleotide sequence of SEQ ID NO: 18; and
   (xii) a cDNA molecule consisting of the nucleotide sequence of SEQ ID NO: 19.

* * * * *

SEQUENCE LISTING

```
<160> NUMBER OF SEQ ID NOS: 23

<210> SEQ ID NO 1
<211> LENGTH: 3435
<212> TYPE: DNA
<213> ORGANISM: Homo sapiens

<400> SEQUENCE: 1
acagcaacta tgaaataatc gtagtatgag aggcagagat cggggcgaga caatggggat      60
gtgggcgcgg gagccccgtt ccggcttagc agcacctccc agcccgcag aataaaaccg      120 atcgcgcccc ctccgcgcgc gccctccccc gagtgcggag cgggaggagg cggcggcggc      180
cgaggaggag gaggaggagg ccccggagga ggaggcgttg gaggtcgagg cggaggcgga      240
```

```
ggaggaggag gccgaggcgc cggaggaggc cgaggcgccg gagcaggagg aggccggccg      300
gaggcggcat gagacgagcg tggcggccgc ggctgctcgg ggccgcgctg gttgcccatt      360
gacagcggcg tctgcagctc gcttcaagat ggccgcttgg ctcgcattca tttctgctg      420 aacgactttt aactttcatt gtcttttccg cccgcttcga tcgcctcgcg ccggctgctc      480
tttccgggat ttttatcaa gcagaaatgc atcgaacaac gagaatcaag atcactgagc      540
taaatcccca cctgatgtgt gtgctttgtg gagggtactt cattgatgcc acaaccataa      600
tagaatgtct acattccttc tgtaaaacgt gtattgttcg ttacctggag accagcaagt      660
attgtcctat ttgtgatgtc caagttcaca agaccagacc actactgaat ataaggtcag      720
ataaaactct ccaagatatt gtatacaaat tagttccagg gcttttcaaa aatgaaatga      780
agagaagaag ggatttttat gcagctcatc cttctgctga tgctgccaat ggctctaatg      840
aagatagagg agaggttgca gatgaagata agagaattat aactgatgat gagataataa      900
gcttatccat tgaattcttt gaccagaaca gattggatcg gaaagtaaac aaagacaaag      960
agaaatctaa ggaggaggtg aatgataaaa gatacttacg atgcccagca gcaatgactg     1020
tgatgcactt aagaaagttt ctcagaagta aaatggacat acctaatact ttccagattg     1080
atgtcatgta tgaggaggaa cctttaaagg attattatac actaatggat attgcctaca     1140
tttatacctg gagaaggaat ggtccacttc cattgaaata cagagttcga cctacttgta     1200
aaagaatgaa gatcagtcac cagagagatg gactgacaaa tgctggagaa ctggaaagtg     1260
actctgggag tgacaaggcc aacagcccag caggaggtat tccctccacc tcttcttgtt     1320
tgcctagccc cagtactcca gtgcagtctc ctcatccaca gtttcctcac atttccagta     1380
ctatgaatgg aaccagcaac agccccagcg gtaaccacca atcttctttt gccaatagac     1440
ctcgaaaatc atcagtaaat gggtcatcag caacttcttc tggttgatac ctgagactgt     1500
taaggaaaaa aattttaaac ccctgattta tatagatatc ttcatgccat tacagctttc     1560
tagatgctaa tacatgtgac tatcgtccaa tttgcttct tttgtagtga cattaaattt     1620
ggctataaaa gatggactac atgtgatact cctatggacg ttaattgaaa agaaagattg     1680
ttgttataaa gaattggttt cttggaaagc aggcaagact ttttctctgt gttaggaaag     1740
atgggaaatg gtttctgtaa ccattgtttg gatttggaag tactctgcag tggacataag     1800
cattgggcca tagtttgtta atctcaacta acgcctacat tacattctcc ttgatcgttc     1860
ttgttattac gctgttttgt gaacctgtag aaaacaagtg ctttttatct tgaaattcaa     1920
ccaacggaaa gaatatgcat agaataatgc attctatgta gccatgtcac tgtgaataac     1980
gatttcttgc atatttagcc attttgattc ctgtttgatt tatacttctc tgttgctacg     2040
caaaaccgat caaagaaaag tgaacttcag ttttacaatc tgtatgccta aaagcgggta     2100
ctaccgttta ttttactgac ttgttttaaat gattcgcttt tgtaagaatc agatggcatt     2160
atgcttgttg tacaatgcca tattggtata tgacataaca ggaaacagta ttgtatgata     2220
tatttataaa tgctataaag aaatattgtg tttcatgcat tcagaaatga ttgttaaaat     2280
tctcccaact ggttcgacct ttgcagatac ccataaccta tgttgagcct tgcttaccag     2340
caaagaatat ttttaatgtg gatatctaat tctaaagtct gttccattag aagcaattgg     2400
cacatctttc tatactttat atactttct ccagtaatac atgtttactt taaagattgt     2460
tgcagtgaag aaaaaccttt aactgagaaa tatggaaacc gtcttaattt tccattggct     2520
atgatggaat taatattgta ttttaaaaat gcatattgat cactataatt ctaaaacaat     2580 ttttaaata aaccagcagg ttgctaaaag aaggcatttt atctaaagtt atttaatag     2640
```

```
gtggtatagc agtaattta aatttaagag ttgcttttac agttaacaat ggaatatgcc      2700
ttctctgcta tgtctgaaaa tagaagctat ttattatgag cttctacagg tattttaaa      2760 tagagcaagc atgttgaatt taaaatatga ataaccccac ccaacaattt tcagtttatt      2820
ttttgctttg gtcgaacttg gtgtgtgttc atcacccatc agttatttgt gagggtgttt      2880
attctatatg aatattgttt catgtttgta tgggaaaatt gtagctaaac atttcattgt      2940
ccccagtctg caaagaagc acaattctat tgctttgtct tgcttatagt cattaaatca       3000
ttacttttac atatattgct gttacttctg ctttctttaa aaatatagta aaggatgttt      3060
tatgaagtca caagatacat atatttttat tttgacctaa atttgtacag tcccattgta      3120
agtgttgttt ctaattatag atgtaaaatg aaatttcatt tgtaattgga aaaaatccaa      3180
taaaaaggat attcatttag aaaatagcta agatctttaa taaaaatttg atatgaaaag      3240
cacaatgtgc agaagttatg gaaaacctat agaggattac aacaggtaaa cgttaaagag      3300
aatacattgc tgacttatag tgatgtggct aagaagtaca tgctttgttg taaaattgct      3360
tgaaagccca ttgaaagatg tatctgtttta tttacagtct ttgaagtaaa agttaccaat    3420
gtttgccaat aaaaa                                                      3435

<210> SEQ ID NO 2
<211> LENGTH: 5989
<212> TYPE: DNA
<213> ORGANISM: Homo sapiens

<400> SEQUENCE: 2
gcgtcccggg tcccgcgcc gcgccgcgac ctgcagaccc cgccgccgcg ctcgggcccg        60
tctcccacgc ccccgccgcc ccgcgcgccc aactccgccg gccgcccgc cccgccccgc       120 gcgctccaga ccccgggggc ggctgccggg agagatgctg gaagaaactt cttaaatgac      180
cgcgtctggc tggccgtgga gccttttctgg gttggggaga ggaaaggaaa gtggaaaaaa    240
cctgagaact tcctgatctc tctcgctgtg agacatgtct gagactcctg ctcagtgtag     300
cattaagcag gaacgaattt catatacacc tccagagagc ccagtgccga gttacgcttc     360
ctcgacgcca cttcatgttc cagtgcctcg agcgctcagg atggaggaag actcgatccg     420
cctgcctgcg cacctgcgct tgcagccaat ttactggagc agggatgacg tagcccagtg     480
gctcaagtgg gctgaaaatg agttttcttt aaggccaatt gacagcaaca cgtttgaaat    540
gaatggcaaa gctctcctgc tgctgaccaa agaggacttt cgctatcgat ctcctcattc     600
aggtgatgtg ctctatgaac tccttcagca tattctgaag cagaggaaac ctcggattct     660
tttttcacca ttcttccacc ctggaaactc tatacacaca cagccggagg tcatactgca    720
tcagaaccat gaagaagata actgtgtcca gaggacccccc aggccatccg tggataatgt    780
gcaccataac cctcccacca ttgaactgtt gcaccgctcc aggtcaccta tcacgacaaa    840
tcaccggcct tctcctgacc ccgagcagcg gcccctccgg tcccccctgg acaacatgat    900
ccgccgcctc tcccggctg agagagctca gggacccagg ccgcaccagg agaacaacca     960
ccaggagtcc taccctctgt cagtgtctcc catggagaat aatcactgcc cagcgtcctc    1020
cgagtcccac ccgaagccat ccagccccg gcaggagagc acacgcgtga tccagctgat     1080
gcccagcccc atcatgcacc ctctgatcct gaaccccccgg cactccgtgg atttcaaaca    1140
gtccaggctc tccgaggacg ggctgcatag ggaaggagag cccatcaacc tctctcatcg    1200
ggaagacctg gcttacatga accacatcat ggtctctgtc tccccgcctg aagagcacgc    1260
```

-continued

```
catgcccatt gggagaatag cagactgtag actgctttgg gattacgtct atcagttgct    1320
ttctgacagc cggtacgaaa acttcatccg atgggaggac aaagaatcca aaatattccg    1380
gatagtggat cccaacggac tggctcgact gtggggaaac cataagaaca gaacaaacat    1440
gacctatgag aaaatgtcca gagccctgcg ccactactac aaactaaaca ttatcaggaa    1500
ggagccagga caaaggcttt tgttcaggtt tatgaaaacc ccagatgaaa tcatgagtgg    1560
ccgaacagac cgtctggagc acctagagtc ccaggagctg gatgaacaaa tataccaaga    1620
agatgaatgc tgaaggaacc aacagtccac ctcagcgggc cagcagccca gggaacccct    1680
gcccaccagg attgctggaa gtgtgacgga gcaggcgggc tgaggagagt ggaaaaggaa    1740
gcgacccaga aatggcaggg acacttctct tgcagaccaa gagggaccct ggagcacctt    1800
agacaaacta cccagcacag gcggggctgg aattctggcg gagggcatga gcctgggact    1860
ccatgtcacg tttccttctg atttggaatc tctccatctg taattcctca ccctcaccct    1920
tccaccgttg ttagtatcat ggtgtttttg ttttgtttt tgttttaaga acctgcagtt     1980
tgactcttca tcgttcatct agggaagac atctgatgtt gttttcctat ggaaatatat    2040
atctattata tatatatttt ttgcaaatct cacaaagtgc ggcaagccca gctggtcagg    2100
aaagagaata cttgcagagg ggttcaggtt cctcttttc ctgccacgtg gatcaggtct    2160
gttcctgtta ctgttgggtc ttggctgaaa aaaaaaatg cttttaaaaa agataaaatg    2220
aaaaggagag ctctcttttt ctctctcttg ctctgttctt cccttggtcc cctctgtcct    2280
cccgccctgc ctgcagttga gattcagatg ccttctgaca gagttcagcc tcttggagag    2340
tcttggggat tgttggcacc taaacagaat cagtgacccg ggtgctttgt ggccagcagc    2400
acagaatcaa acccgcatcc cagcattggg ccacccatct gagggaggcc aaaatcatca    2460
cagatgctgc tgtgctgcag acagatacat gctagtccag agagccgccc ctagatggc     2520 tgtgagaacc atgtgtctaa ggcgtaagat aaggatggaa ggctgtccaa gttatttgga    2580
aggcctcggc agcttgggat tagcttggga gcgcagcgct gcaaagtgga aaatatgaaa    2640
agaccacaca ggcccagcag tccagaaact gggcaaaaat attctgcagt ggggatttat    2700
ttttccaaag caggtaacag aggctagtga gaaagaaaag ctcctctctg ctccattcca    2760
aaggccatct tgtggtcagt ttcatgccct cacctgattt ttttttttt ttttttttt     2820 caattcctaa cctttttaa agtttcctgg tctccactgg acacagagct ttggagacgg     2880
aggatcccag agggcagtct cagttgcaat cagtgtgtgc ccagcctggg cagacaggaa    2940
attcctcgga tacattattt tttctttctt tcatagctgt gtctcagaaa ggacccattt    3000
gtggctcttt ttcacctcaa aataagatcg atggtatctt gtaaaatgag ggtagtgcca    3060
cttcttagta ttttgaaag ctgttttaga ttttttttt tttcctttt ctagccatct      3120 aaattgactc ttccaatata ggtctcagaa atccaatatt tggagtacaa tttctttaa    3180 tccagattac acctgcctta caaagcaccc cctccttgtt ccctctgtt tcctctactc    3240 agttggggga gaaactcaca gctcctccgg gatacatatg tgccctcagc agcagctccc    3300
aggtgaagtt accagacccc tgggcttctc cccagctttt tctgagttga gtcagacatg    3360
tagagtttgg gtcacacagg caagaggaat tttccctcgg ccttactgac aaggacacca    3420
acctagggtg caaacagatg gactatggtt caaggacact ggaattgagg agctgatcaa    3480
ggctctcttc agccttgctc tgtccctgcc tcttatcaga gcacaggtag acacacgggc    3540
atagccagcc cactcctact gtcacaggcg ccccaccatt caaccttccg ggaggtcagg    3600
gaccttctat atgaggcgag tgggtctcag tctgcttgaa tggtgatgag attctgctgg    3660
```

```
atctcagcac gctgcaggtg tcttttgaga gcattcagta ggacatggtg atccctattt   3720
cagcctctaa gatgactggt attctatctg aaatgcagag attaagccaa atacctgatg   3780
tattgtgaaa gccactgatt ttaagaatgg agagaaaggg attttttact gcatccctct   3840
gtatgaatat gaaatcagag accagggcat gatgttgcta ggattagagc ctctcagtct   3900
ggcctcttca cccaagtgca agaactcagt ctcttactgt tcaaagaatc ttaacagttg   3960
aattatggag ggaaattccc ttttgcccca agcatttcta tatttaaagc aatatcccag   4020
gagaatatgt tagacttagg atgatacctt cagccacttg aagaagaaat agaaggcgct   4080
cattccaata tagtctttat ttcccattca gatacaggtt gagcatccct aatctgaaca   4140
gttaaaaccc ccaaatgccc caaaatccaa accttcctga acgctatgac accatgagtg   4200
gaaaattcca cacctaacaa acacatttgc tttcttatgg ttcaatgtac acaaactgtt   4260
ttatatagaa aatgatttca aatatcataa aattccttca aggctatgtg tataaagtat   4320
atatgagcca taaatgaatt ttgtgtttag actttgtgtc catccccaag atctctcatt   4380
ttatatatat atatatatat atatatatat atatatatat atatatatac acacacacac   4440
acatacacaa atattccagg atacaaaaaa aaacatttaa aaatccgaga cccagaacac   4500
ttctggtccc aagcatttca gataagggat atcaatctgt actaccaata aggatttcgt   4560
aattccccta actgcaaatg tcctcttcat ttgttcttta tgagaaaacc cgggtagtgc   4620
cagcacctgg atacagtatt tacaccctgc agaccctaaa gatttcagat tcagttagca   4680
aaccttgatg aagcacctgc tggacactga gggacccaaa gctcaatcag ccataatccc   4740
tgctttcaga gtttatattg tacctgccta atccacccgg cgtgactcat ttcaacacta   4800
agtactaggg gtgttgtcag gagacaaatc tgaagtcagg agaggaaaat gcaaaggagc   4860
cctgccgtgt gatggatgtg cattctcact tgggtcttga agttctcatt cctacatctc   4920
aagctagcca ggcagtctcc tctctatcag aagaaagcac tggtaattgg ctagactggc   4980
tatgttgaag gtaacatgaa ctctaagatc ttgacccagg gcgacttggt tttgcttaag   5040
gtggcatcac caatgttcca aatcctttag ggagatgagg gtatcccac agaaaaagag   5100 gaataataga ccaatggatt ttctcctttc accagtatgt ttggaaccct ctgatccaat   5160
gtcttttgat actgatctct tgtccaaatg agaatgtcgc tttagctgaa attcaaatgg   5220
ctgtgacaat ttaccgaaat gatgaagtaa ccaccattcc cacctttcac tgcctaggct   5280
ccaagtctga atacattttt gaaataggaa ctcccttttg caaaaagaa acctgggtgt   5340 cagggaggtg aagtgacttg ccctaggagc agacagcatg ccaagaatgg aattaggctc   5400
aggatccagc ctgggctcac cctgtgtggc tcattcccac ccaggaaact gaagataaaa   5460
gatttgggaa aacacaccaa gaaaaagggg cagttttctt tgcccaagca tttggtgcta   5520
gttagaggct gttcactctc tcctgctcct cttcggagta gaaataaagg ctgtgacaca   5580
aggaagccag tggggtggga gggaggcacc ataatccctc cctaaaaccc acagaagact   5640
aacctgatac tcttttgacc caactgcatc aacactaaac agctgcagac cccctgaatc   5700
tttcacacat gccaagtgaa cattcttgat gatttctctt tgtgaccgca accacctgca   5760
aaccagaacg actctagaat ttccttcccc gccccccttt ttgtttagtt tctaatctct   5820
tgtttatgag gtgtggggtt tataagggac tgaatcaaat gaatgtaaca aaaagaaaa   5880 aaaaaacaaa aaaaaatgcc ttttctcagg gccagtgagt tgcaaataat ttttaaagaa   5940
aagcctataa ttacatcatc tcaataaatt ttttataaaa aaaaaaaa              5989
```

<210> SEQ ID NO 3
<211> LENGTH: 2753
<212> TYPE: DNA
<213> ORGANISM: Homo sapiens

<400> SEQUENCE: 3

| | | | | | |
|---|---|---|---|---|---|
| gagcgcagag | cggtttggtc | gttcgttggg | cggtgctggt | ttttcgctcg | tcgactgcgg | 60 |
| ctcttcctcg | ggcagcggaa | gcggcgcggc | ggtcggagaa | gtggcctaaa | acttcggcgt | 120 |
| tgggtgaaag | aaaatggccc | gaaccaagca | gactgctcgt | aagtccaccg | gtgggaaagc | 180 |
| cccccgcaaa | cagctggcca | cgaaagccgc | caggaaaagc | gctccctcta | ccggcggggt | 240 |
| gaagaagcct | catcgctaca | ggcccgggac | cgtggcgctt | cgagagattc | gtcgttatca | 300 |
| gaagtcgacc | gagctgctca | tccggaagct | gcccttccag | aggttggtga | gggagatcgc | 360 |
| gcaggatttc | aaaaccgacc | tgaggtttca | gagcgcagcc | atcggtgcgc | tgcaggaggc | 420 |
| tagcgaagcg | tacctggtgg | gtctgttcga | agataccaac | ctgtgtgcca | tccacgctaa | 480 |
| gagagtcacc | atcatgccca | agacatcca | gttggctcgc | cggatacggg | agagagagc | 540 |
| ttaagtgaag | gcagttttta | tggcgttttg | tagtaaattc | tgtaaaatac | tttggtttaa | 600 |
| tttgtgactt | ttttttgtaag | aaattgttta | taatatgttg | catttgtact | taagtcattc | 660 |
| catctttcac | tcaggatgaa | tgcgaaaagt | gactgttcac | agacctcagt | gatgtgagca | 720 |
| ctgttgctca | ggagtgacaa | gttgctaata | tgcagaaggg | atgggtgata | cttcttgctt | 780 |
| ctcatgatgc | atgtttctgt | atgttaatga | cttgttgggt | agctattaag | gtactagagt | 840 |
| tgataaatgt | gtacagggtc | cttttgcaat | aaaactggtt | atgacttgat | ccaagtgttt | 900 |
| aacaattggg | gctgttaagt | ctgaccatac | atcactgtga | tagaatgtgg | gcttttttcaa | 960 |
| gggtgaagat | acaagtctta | accacagtgt | aacttacagt | ttccttttaaa | aaaaaaaaaa | 1020 |
| gtaaacctgg | cagctataga | atacactatg | tgcatttata | atagctatttt | tatatattgt | 1080 |
| agtatcaaca | ttttttaaatt | aaatgttttta | cattcacaag | tggtggggag | tcttgtcatt | 1140 |
| aaggtgtgtg | taatttagag | tccagttggt | tttcttctga | ctgcacttgt | tctcatagta | 1200 |
| gtaaaatgct | atgcgcattt | ataccttgca | taagtcctca | ttctaccaca | tgttaaccct | 1260 |
| ctagctgata | atgcaaacac | taactggggg | attttattta | taagggctct | agaaaaaacg | 1320 |
| agttattcac | accagcatca | tcttaactaa | cattctgaac | tagttagtgc | agcttttcat | 1380 |
| tgtgttgtgt | ggttggtctc | ataactaggt | tgagttttttc | tcctctgctg | aggaaacagt | 1440 |
| accgaagttc | ttttttcttgt | ggcatttgta | ttataaaaac | ttggtgtggg | ggaggagcac | 1500 |
| aaaactccag | cccactgaac | ctctgccaat | taagatggtg | ttgggttagg | ttacatctgg | 1560 |
| ttactgtcct | gggaaaatca | ttttttataga | gatggccttc | caagtggttt | taaaatttac | 1620 |
| tgaagttttt | aggtcaatta | tgtatgttga | ctaaatttac | aaataaactt | gtttatccaa | 1680 |
| ctaagtgtcc | aaaacctaaa | ttgaatgtac | taagttttca | catgtcccat | tatctaggtc | 1740 |
| cttgtatact | aatgttttga | acttagatca | tttcaggtgt | tgtttggtgg | ataaaggaac | 1800 |
| cttttatttta | taaagatact | gtagaaagca | tgtgaacagc | tctctgcttg | attaagatgc | 1860 |
| cataatagtg | ctgtatttgc | agtgtgggct | aagacaaagt | atattaataa | gcttttcagc | 1920 |
| cccccactc | ccgttccgta | gtgtagaagc | ccacaggtgt | agaactcagt | cttaaacttc | 1980 |
| agtatgaaac | cagtttcctt | gtgcgatgat | ggccactaaa | gcatagtacg | tggatgtcag | 2040 |
| tgagacagca | tgagagccag | cagtcatcaa | agcgttccac | gtttgaagtt | agcaactgct | 2100 |
| taaagttatg | cccctattaaa | attgcttctct | caaaagtttg | ggttagtttc | aaatgtgata | 2160 |

| | |
|---|---|
| ttttggaggg aaggtaaagt aggtatctttt caggtcgtga taatgagctc ctatgaaagg | 2220 |
| atgcaatata atgacccgct tttctagaaa gttcataatc agctctggaa caagcacact | 2280 |
| tgattcctca ctgtgcttca gaatgagatt aagatcagat gttggaacgt gctatgctgt | 2340 |
| agcgtgtctg gaaacaaagt acacaaacct ggctacggtg atgagttagc ttctgcttac | 2400 |
| tacctgtgac aacccaagtg ggtgacacta gtgaaccttc tccagtctgc aggctggcat | 2460 |
| agaaggctct tagattatat tgggcagctt gcaatctgcc gaagcagtga cttgcatttc | 2520 |
| cacacttggc ttgagcactc aacccagaag gcgaagatag cttttggttg taggcggctt | 2580 |
| cctgtatggg atatccctcg gtaagggtaa aggagcagag gcaaggagaa aaagcagaag | 2640 |
| ttgcagctga tgcaggtatc ctatgccctt gatggatgag actaaaataa aattttgaa | 2700 |
| gttaaaaaaa aaaaaaaaa aaaaaaaaa aaaaaaaaa aaa | 2753 |

<210> SEQ ID NO 4
<211> LENGTH: 672
<212> TYPE: DNA
<213> ORGANISM: Homo sapiens

<400> SEQUENCE: 4

| | |
|---|---|
| gagagagagc gagagaacta gtctcgagtt tttttttttt tttttttttt tttttttttt | 60 |
| tttttttttt tttccagccc cggtaccgga ccctgcagcc gcagagatgt tgatgcctaa | 120 |
| aaaaaaccgg attgccattt atgaactcct tttaaggag ggagtcatgg tggccaagaa | 180 |
| ggatgtccac atgcctaagc acccggagct ggcagacaag aatgtgccca accttcatgt | 240 |
| catgaaggcc atgcagtctc tcaagtcccg aggctacgtg aaggaacagt ttgcctggag | 300 |
| acatttctac tggtaccctta ccaatgaggg tatccagtat ctccgtgatt accttcatct | 360 |
| gccccggag attgtgcctg ccaccctacg ccgtagccgt ccagagactg gcaggcctcg | 420 |
| gcctaaaggt ctggagggtg agcgacctgc gagactcaca agaggggaag ctgacagaga | 480 |
| tacctacaga cggagtgctg tgccacctgg tgccgacaag aaagccgagg ctggggctgg | 540 |
| gtcagcaacc gaattccagt ttagaggcgg atttggtcgt ggacgtggtc agccacctca | 600 |
| gtaaaattgg agaggattct tttgcattga ataaacttac agccaaaaaa ccttaaaaaa | 660 |
| aaaaaaaaaa aa | 672 |

<210> SEQ ID NO 5
<211> LENGTH: 3677
<212> TYPE: DNA
<213> ORGANISM: Homo sapiens

<400> SEQUENCE: 5

| | |
|---|---|
| tcgcggaggc ttggggcagc cgggtagctc ggaggtcgtg gcgctggggg ctagcaccag | 60 |
| cgctctgtcg ggaggcgcag cggttaggtg gaccggtcag cggactcacc ggccagggcg | 120 |
| ctcggtgctg gaatttgata ttcattgatc cgggttttat ccctcttctt ttttcttaaa | 180 |
| cattttttt taaaactgta ttgtttctcg ttttaattta ttttgcttg ccattcccca | 240 |
| cttgaatcgg gccgacggct tggggagatt gctctacttc cccaaatcac tgtggatttt | 300 |
| ggaaccagc agaagagga aagagtagc aagagctcca gagagaagtc gaggaagaga | 360 |
| gagacggggt cagagagagc gcgcgggcgt gcgagcagcg aaagcgacag gggcaaagtg | 420 |
| agtgacctgc ttttgggggt gaccgccgga gcgcggcgtg agccctcccc cttgggatcc | 480 |
| cgcagctgac cagtcgcgct gacggacaga cagacagaca ccgcccccag ccccagctac | 540 |

```
cacctcctcc ccggccggcg gcggacagtg gacgcggcgg cgagccgcgg gcaggggccg    600
gagcccgcgc ccggaggcgg ggtggagggg gtcggggctc gcggcgtcgc actgaaactt    660
ttcgtccaac ttctgggctg ttctcgcttc ggaggagccg tggtccgcgc ggggggaagcc   720
gagccgagcg gagccgcgag aagtgctagc tcgggccggg aggagccgca gccggaggag    780
ggggaggagg aagaagagaa ggaagaggag aggggccgc agtggcgact cggcgctcgg     840
aagccgggct catggacggg tgaggcgcg gtgtgcgcag acagtgctcc agccgcgcgc     900
gctccccagg ccctggcccg ggcctcgggc cggggaggaa gagtagctcg ccgaggcgcc    960
gaggagagcg ggccgcccca cagcccgagc cggagaggga gcgcgagccg cgccggcccc    1020
ggtcgggcct ccgaaaccat gaactttctg ctgtcttggg tgcattggag ccttgccttg    1080
ctgctctacc tccaccatgc caagtggtcc caggctgcac ccatggcaga aggaggaggg    1140
cagaatcatc acgaagtggt gaagttcatg gatgtctatc agcgcagcta ctgccatcca    1200
atcgagaccc tggtggacat cttccaggag taccctgatg agatcgagta catcttcaag    1260
ccatcctgtg tgcccctgat gcgatgcggg ggctgctgca atgacgaggg cctggagtgt    1320
gtgcccactg aggagtccaa catcaccatg cagattatgc ggatcaaacc tcaccaaggc    1380
cagcacatag agagatgag cttcctacag cacaacaaat gtgaatgcag accaaagaaa    1440
gatagagcaa gacaagaaaa aaaatcagtt cgaggaaagg gaaaggggca aaaacgaaag    1500
cgcaagaaat cccggtataa gtcctggagc gtgtacgttg tgcccgctg ctgtctaatg     1560
ccctggagcc tccctggccc ccatccctgt gggccttgct cagagcggag aaagcatttg    1620
tttgtacaag atccgcagac gtgtaaatgt tcctgcaaaa acacagactc gcgttgcaag    1680
gcgaggcagc ttgagttaaa cgaacgtact tgcagatgtg acaagccgag gcggtgagcc    1740
gggcaggagg aaggagcctc cctcagggtt tcgggaacca gatctctcac caggaaagac    1800
tgatacagaa cgatcgatac agaaaccacg ctgccgccac cacaccatca ccatcgacag    1860
aacagtcctt aatccagaaa cctgaaatga aggaagagga gactctgcgc agagcacttt    1920
gggtccggag ggcgagactc cggcggaagc attcccgggc gggtgaccca gcacggtccc    1980
tcttggaatt ggattcgcca tttttatttt cttgctgcta aatcaccgag cccggaagat    2040
tagagagttt tatttctggg attcctgtag acacacccac ccacatacat acatttatat    2100
atatatatat tatatatata taaaaataaa tatctctatt ttatatatat aaaatatata    2160
tattctttt ttaaattaac agtgctaatg ttattggtgt cttcactgga tgtatttgac     2220
tgctgtggac ttgagttggg aggggaatgt tcccactcag atcctgacag gaagaggag     2280
gagatgagag actctggcat gatctttttt ttgtcccact tggtggggcc agggtcctct    2340
cccctgccca ggaatgtgca aggccagggc atggggcaa atatgaccca gttttgggaa     2400
caccgacaaa cccagccctg cgctgagcc tctctacccc aggtcagacg acagaaaga     2460
cagatcacag gtacagggat gaggacaccg gctctgacca ggagtttggg gagcttcagg    2520
acattgctgt gctttgggga ttccctccac atgctgcacg cgcatctcgc ccccaggggc    2580
actgcctgga agattcagga gcctgggcgg ccttcgctta ctctcacctg cttctgagtt    2640
gcccaggaga ccactggcag atgtcccggc gaagagaaga gacacattgt tggaagaagc    2700
agcccatgac agctccccctt cctgggactc gccctcatcc tcttcctgct ccccttcctg    2760
gggtgcagcc taaaaggacc tatgtcctca caccattgaa accactagtt ctgtcccccc    2820
aggagacctg gttgtgtgtg tgtgagtggt tgaccttcct ccatccctg gtccttccct     2880
tcccttcccg aggcacagag agacagggca ggatccacgt gcccattgtg gaggcagaga    2940
```

```
aaagagaaag tgttttatat acggtactta tttaatatcc cttttttaatt agaaattaaa      3000 acagttaatt taattaaaga gtagggtttt ttttcagtat tcttggttaa tatttaattt      3060
caactattta tgagatgtat cttttgctct ctcttgctct cttatttgta ccggttttg       3120 tatataaaat tcatgtttcc aatctctctc tccctgatcg gtgacagtca ctagcttatc      3180
ttgaacagat atttaatttt gctaacactc agctctgccc tccccgatcc cctggctccc      3240
cagcacacat tcctttgaaa taaggtttca atatacatct acatactata tatatatttg      3300
gcaacttgta tttgtgtgta tatatatata tatatgttta tgtatatatg tgattctgat      3360
aaaatagaca ttgctattct gttttttata tgtaaaaaca aaacaagaaa aaatagagaa      3420
ttctacatac taaatctctc tccttttta  attttaatat ttgttatcat ttatttattg      3480
gtgctactgt ttatccgtaa taattgtggg gaaaagatat taacatcacg tctttgtctc      3540
tagtgcagtt tttcgagata ttccgtagta catatttatt tttaaacaac gacaaagaaa      3600
tacagatata tcttaaaaaa aaaaaagcat tttgtattaa agaatttaat tctgatctca      3660
aaaaaaaaaa aaaaaaa                                                     3677

<210> SEQ ID NO 6
<211> LENGTH: 2729
<212> TYPE: DNA
<213> ORGANISM: Homo sapiens

<400> SEQUENCE: 6
ggcggccgag caccgagcgc tgggcaccgg gcaccgagcg gcggcggcac gcgaggcccg        60
gccccgagca gcgcccccgc ccgccgcggc ctccagcccg gccccgccca gcgccggccc       120
gcggggatgc ggagcggcgg gcgcggagg ccgcggcccg gctaggcccg cgctcgcgcc        180
cggacgcggc ggcccgaggc tgtggccagg ccagctgggc tcggggagcg ccagcctgag       240
aggagcgcgt gagcgtcgcg ggagcctcgg gcaccatgag cgacgtggct attgtgaagg       300
agggttggct gcacaaacga ggggagtaca tcaagacctg gcggccacgc tacttcctcc       360
tcaagaatga tggcaccttc attggctaca aggagcggcc gcaggatgtg gaccaacgtg       420 aggctccccct caacaacttc tctgtggcgc agtgccagct gatgaagacg gagcggcccc      480
ggcccaacac cttcatcatc cgctgcctgc agtggaccac tgtcatcgaa cgcaccttcc       540
atgtggagac tcctgaggag cgggaggagt ggacaaccgc catccagact gtggctgacg       600
gcctcaagaa gcaggaggag gaggagatgg acttccggtc gggctcaccc agtgacaact       660 cagggggctga agagatggag gtgtccctgg ccaagcccaa gcaccgcgtg accatgaacg      720
agtttgagta cctgaagctg ctgggcaagg gcactttcgg caaggtgatc ctggtgaagg       780
agaaggccac aggccgctac tacgccatga agatcctcaa gaaggaagtc atcgtggcca       840
aggacgaggt ggcccacaca ctcaccgaga accgcgtcct gcagaactcc aggcacccct       900
tcctcacagc cctgaagtac tcttttccaga cccacgaccg cctctgcttt gtcatggagt       960
acgccaacgg gggcgagctg ttcttccacc tgtcccggga gcgtgtgttc tccgaggacc      1020
gggcccgctt ctatggcgct gagattgtgt cagccctgga ctacctgcac tcggagaaga     1080
acgtggtgta ccgggacctc aagctggaga acctcatgct ggacaaggac gggcacatta     1140
agatcacaga cttcgggctg tgcaaggagg ggatcaagga cggtgccacc atgaagacct     1200
tttgcggcac acctgagtac ctggcccccg aggtgctgga ggacaatgac tacgccgtg      1260 cagtggactg gtgggggctg ggcgtggtca tgtacgagat gatgtgcggt cgcctgcct     1320
```

```
tctacaacca ggaccatgag aagcttttg agctcatcct catggaggag atccgcttcc    1380
cgcgcacgct tggtcccgag gccaagtcct tgctttcagg gctgctcaag aaggacccca    1440
agcagaggct tggcggggc tccgaggacg ccaaggagat catgcagcat cgcttctttg    1500
ccggtatcgt gtggcagcac gtgtacgaga agaagctcag cccacccttc aagcccagg     1560 tcacgtcgga gactgacacc aggtattttg atgaggagtt cacggcccag atgatcacca    1620
tcacaccacc tgaccaagat gacagcatgg agtgtgtgga cagcgagcgc aggcccact     1680 tccccccagtt ctcctactcg gccagcggca cggcctgagg cggcggtgga ctgcgctgga    1740
cgatagcttg gagggatgga gaggcggcct cgtgccatga tctgtattta atggttttta    1800
tttctcgggt gcatttgaga aagccacgc tgtcctctcg agcccagatg aaagacgtt     1860 tttgtgctgt gggcagcacc ctcccccgca gcggggtagg aagaaaact atcctgcggg    1920 ttttaattta tttcatccag tttgttctcc gggtgtggcc tcagccctca gaacaatccg    1980
attcacgtag ggaaatgtta aggacttctg cagctatgcg caatgtggca ttgggggcc    2040 gggcaggtcc tgcccatgtg tccctcact ctgtcagcca gccgcctgg gctgtctgtc    2100 accagctatc tgtcatctct ctggggccct gggcctcagt tcaacctggt ggcaccagat    2160
gcaacctcac tatggtatgc tggccagcac cctctcctgg gggtggcagg cacacagcag    2220
ccccccagca ctaaggccgt gtctctgagg acgtcatcgg aggctgggcc ctgggatgg     2280 gaccagggat gggggatggg ccagggttta cccagtggga cagaggagca aggtttaaat    2340
ttgttattgt gtattatgtt gttcaaatgc attttgggg ttttaatct ttgtgacagg     2400 aaagccctcc cccttcccct tctgtgtcac agttcttggt gactgtccca ccgggagcct    2460 cccctcaga tgatctctcc acggtagcac ttgacctttt cgacgcttaa cctttccgct    2520
gtcgccccag gccctccctg actccctgtg ggggtggcca tccctgggcc cctccacgcc    2580
tcctggccag acgctgccgc tgccgctgca ccacggcgtt tttttacaac attcaacttt    2640
agtattttta ctattataat ataatatgga accttccctc caaattcttc aataaaagtt    2700
gcttttcaaa aaaaaaaaaa aaaaaaaa                                       2729
```

<210> SEQ ID NO 7
<211> LENGTH: 1680
<212> TYPE: DNA
<213> ORGANISM: Homo sapiens

<400> SEQUENCE: 7

```
gagacggcgg cggctgtagc ggcgtgacag gagcccatg gcacctgccc agccccacct      60
cagcccatct tgacaaaatc taaggctcca tggagccacc acggggcccc cctgccaatg    120
gggccgagcc atcccgggca gtgggcaccg tcaaagtata cctgcccaac aagcaacgca    180
cggtggtgac tgtccgggat ggcatgagtg tctacgactc tctagacaag gccctgaagg    240 tgcgggtct aaatcaggac tgctgtgtgg tctaccgact catcaaggga cgaaagacgg    300
tcactgcctg ggacacagcc attgctcccc tggatggcga ggagctcatt gtcgaggtcc    360
ttgaagatgt cccgctgacc atgcacaatt ttgtacggaa gaccttcttc agcctggcgt    420
tctgtgactt ctgccttaag tttctgttcc atggcttccg ttgccaaacc tgtggctaca    480
agttccacca gcattgttcc tccaaggtcc ccacagtctg tgttgacatg agtaccaacc    540
gccaacagcc ctcaaggttc taccacagtg tccaggattt gtccggaggc tccagacagc    600
atgaggctcc ctcgaaccgc ccctgaatg agttgctaac cccccagggt cccagccccc    660
gcacccagca ctgtgacccg gagcacttcc ccttccctgc cccagccaat gccccctac     720
```

| | |
|---|---|
| agcgcatccg ctccacgtcc actcccaacg tccatatggt cagcaccacg gcccccatgg | 780 |
| actccaacct catccagctc actggccaga gtttcagcac tgatgctgcc ggtagtagag | 840 |
| gaggtagtga tggaaccccc cgggggagcc ccagcccagc cagcgtgtcc tcggggagga | 900 |
| agtccccaca ttccaagtca ccagcagagc agcgcgagcg gaagtccttg gccgatgaca | 960 |
| agaagaaagt gaagaacctg ggtaccgggg actcaggcta ttactgggag gtaccaccca | 1020 |
| gtgaggtgca gctgctgaag aggatcggga cgggctcgtt tggcaccgtg tttcgagggc | 1080 |
| ggtggcatgg cgatgtggcc gtgaaggtgc tcaaggtgtc ccagcccaca gctgagcagg | 1140 |
| cccaggcttt caagaatgag atgcaggtgc tcaggaagac gcgacatgtc aacatcttgc | 1200 |
| tgtttatggg cttcatgacc cggccgggat tgccatcat cacacagtgg tgtgagggct | 1260 |
| ccagcctcta ccatcacctg catgtggccg acacacgctt cgacatggtc cagctcatcg | 1320 |
| acgtggcccg gcagactgcc cagggcatgg actacctcca tgccaagaac atcatccacc | 1380 |
| gagatctcaa gtctaacaac atcttcctac atgaggggct cacggtgaag atcggtgact | 1440 |
| ttggcttggc cacagtgaag actcgatgga gcggggccca gcccttggag cagccctcag | 1500 |
| gatctgtgct gtggatggca gctgaggtga tccgtatgca ggacccgaac ccctacagct | 1560 |
| tccagtcaga cgtctatgcc tacggggttg tgctctacga gcttatgact ggctcactgc | 1620 |
| cttacagcca cattggctgc cgtgaccaga ttatctttat ggtgggccgt ggctatctgt | 1680 |

<210> SEQ ID NO 8
<211> LENGTH: 1216
<212> TYPE: DNA
<213> ORGANISM: Homo sapiens

<400> SEQUENCE: 8

| | |
|---|---|
| ctcattgact tccttcctgt tctaactgcc agtactcaga agtcagagtt gagagacaga | 60 |
| ggcaccccgg acagagacgt gaagcactga ataaatagat cagaatgact gaaaaagccc | 120 |
| cagagccaca tgtggaggag gatgatgatg atgagctgga cagcaagctc aattataagc | 180 |
| ctccaccaca gaagtccctg aaagagctgc aggaaatgga caaagatgat gagagtctaa | 240 |
| ttaagtacaa gaaaacgctg ctgggagatg gtcctgtggt gacagatccg aaagccccca | 300 |
| atgtcgttgt cacccggctc accctggttt gtgagagtgc cccgggacca atcaccatgg | 360 |
| accttactgg agatctggaa gccctcaaaa aggaaaccat tgtgttaaag gaaggttctg | 420 |
| aatatagagt caaaattcac ttcaaagtga cagggatat tgtgtcaggc ctgaaatacg | 480 |
| ttcagcacac ctacaggact gggtgaaag tggataaagc aacatttatg gttggcagct | 540 |
| atggacctcg gcctgaggag tatgagttcc tcactccagt tgaggaggct cccaagggca | 600 |
| tgctggcgcg aggcacgtac cacaacaagt ccttcttcac cgacgatgac aagcaagacc | 660 |
| acctcagctg ggagtggaac ctgtcgatta agaaggagtg gacagaatga atgcatccac | 720 |
| cccttccccc acccttgcca cctggaagaa ttctctcagg cgtgttcagc accctgtccc | 780 |
| tcctcctgt ccacagctgg gtccctcttc aacactgcca catttcctta ttgatgcatc | 840 |
| ttttcccacc ctgtcactca acgtggtccc tagaacaaga ggcttaaaac cgggctttca | 900 |
| cccaacctgc tccctctgat cctccatcag ggccagatct tccacgtctc catctcagta | 960 |
| cacaatcatt taatatttcc ctgtcttacc cctattcaag caactagagg ccagaaaatg | 1020 |
| ggcaaattat cactaacagg tctttgactc aggttccagt agttcattct aatgcctaga | 1080 |
| ttcttttgtg gttgttgctg gcccaatgag tccctagtca catcccctgc cagagggagt | 1140 |

```
tcttcttttg tgagagacac tgtaaacgac acaagagaac aagaataaaa caataactgt    1200
gtgtgttctg gctgag                                                   1216

<210> SEQ ID NO 9
<211> LENGTH: 987
<212> TYPE: DNA
<213> ORGANISM: Homo sapiens

<400> SEQUENCE: 9
aatataagtg gaggcgtcgc gctggcgggc attcctgaag ctgacagcat tcgggccgag     60
atgtctcgct ccgtggcctt agctgtgctc gcgctactct ctctttctgg cctggaggct    120
atccagcgta ctccaaagat tcaggtttac tcacgtcatc cagcagagaa tggaaagtca    180
aatttcctga attgctatgt gtctgggttt catccatccg acattgaagt tgacttactg    240
aagaatggag agagaattga aaaagtggag cattcagact tgtctttcag caaggactgg    300
tctttctatc tcttgtacta cactgaattc accccccactg aaaaagatga gtatgcctgc    360
cgtgtgaacc atgtgacttt gtcacagccc aagatagtta agtgggatcg agacatgtaa    420
gcagcatcat ggaggtttga agatgccgca tttggattgg atgaattcca aattctgctt    480
gcttgctttt taatattgat atgcttatac acttacactt tatgcacaaa atgtagggtt    540
ataataatgt taacatggac atgatcttct ttataattct actttgagtg ctgtctccat    600
gtttgatgta tctgagcagg ttgctccaca ggtagctcta ggagggctgg caacttagag    660
gtggggagca gagaattctc ttatccaaca tcaacatctt ggtcagattt gaactcttca    720
atctcttgca ctcaaagctt gttaagatag ttaagcgtgc ataagttaac ttccaatta    780 catactctgc ttagaatttg ggggaaaatt tagaaatata attgacagga ttattggaaa    840
tttgttataa tgaatgaaac attttgtcat ataagattca tatttacttc ttatacattt    900
gataaagtaa ggcatggttg tggttaatct ggtttatttt tgttccacaa gttaaataaa    960
tcataaaact tgatgtgtta tctctta                                       987

<210> SEQ ID NO 10
<211> LENGTH: 1613
<212> TYPE: DNA
<213> ORGANISM: Homo sapiens

<400> SEQUENCE: 10
gtgacgctgg gcctgcagcg cggagcagaa agcagaaccc gcagagtcct ccctgctgct     60
gtgtggacga cacgtgggca caggcagaag tgggccctgt gaccagctgc actggtttcg    120
tggaaggaag ctccaggact ggcgggatgg gctcagcctg tatcaaagtc accaaatact    180
ttctcttcct cttcaacttg atcttcttta tcctgggcgc agtgatcctg gcttcgggg     240 tgtggatcct ggccgacaag agcagtttca tctctgtcct gcaaacctcc tccagctcgc    300
ttaggatggg ggcctatgtc ttcatcggcg tgggggcagt cactatgctc atgggcttcc    360
tgggctgcat cggcgccgtc aacgaggtcc gctgcctgct ggggctgtac tttgctttcc    420
tgctcctgat cctcattgcc caggtgacgg ccggggccct cttctacttc aacatgggca    480
agctgaagca ggagatgggc ggcatcgtga ctgagctcat tcgagactac aacagcagtc    540
gcgaggacag cctgcaggat gcctgggact acgtgcaggc tcaggtgaag tgctgcggct    600
gggtcagctt ctacaactgg acagacaacg ctgagctcat gaatcgccct gaggtcacct    660
accccctgtt ctgcgaagtc aagggggaag aggacaacag cctttctgtg aggaagggct    720
tctgcgaggc ccccggcaac aggacccaga gtggcaacca ccctgaggac tggcctgtgt    780
```

```
accaggaggg ctgcatggag aaggtgcagg cgtggctgca ggagaacctg ggcatcatcc    840
tcggcgtggg cgtgggtgtg ccatcgtcg agctcctggg gatggtcctg tccatctgct     900
tgtgccggca cgtccattcc gaagactaca gcaaggtccc caagtactga ggcagctgct    960
atccccatct ccctgcctgg cccccaacct cagggctccc aggggtctcc ctggctccct    1020
cctccaggcc tgcctcccac ttcactgcga agaccctctt gcccaccctg actgaaagta    1080
gggggctttc tggggcctag cgatctctcc tggcctatcc gctgccagcc ttgagccctg    1140
gctgttctgt ggttcctctg ctcaccgccc atcagggttc tcttagcaac tcagagaaaa    1200
atgctcccca cagcgtccct ggcgcaggtg ggctggactt ctacctgccc tcaagggtgt    1260
gtatattgta tagggcaac tgtatgaaaa attggggagg aggggccgg gcgcggtggc      1320 tcacgcctgt aatcccagca ctttgggagg ccgaggcggg tggatcacga ggtcaggaga    1380
tcgagaccat cctggctaac atggtgaaac cccgtctcta ctaaaaatac aaaaaaaatt    1440
tagccgggcg cggtggcggg cacctgtagt cccagctact tgggaggctg aggcaggaga    1500
atggtgtgaa cccgggagcg gaggttgcag tgagctgaga tcgtgctact gcactccagc    1560
ctgggggaca gaaagagact ccgtctcaaa aaaaaaaaa aaaaaaaaa aaa             1613
```

<210> SEQ ID NO 11
<211> LENGTH: 2265
<212> TYPE: DNA
<213> ORGANISM: Homo sapiens

<400> SEQUENCE: 11

```
acgcggaggt tgtaattggt tctctagacca cacctagttg ttgagtgccg ctgcttgaaa    60
atctcagttc tgccgagatc gcagaataca cacaagctac ctttgggcac cagagcagac    120
agaaccgcgg agcttcaggg tggaagattc gtggaaactt tgccaaggcc aggacctcgt    180
gtgttcccgt ccgcccctct gggacggcgc cagcccggca ggccgccgac cgtcctgggg    240
ctcccgcgca gcgcgatgcc ggcctcgtcc accgtccacg tgctgcagct gctgcgggag    300
ctgctcgcct tcgtgctcct cagctacacg gtgctcatcg gggcgctgct gctggccggc    360
tggaccactt acttcctggt gctgaagtga cagcgccgtc gccgcgcccg gccccgcctc    420 cgcccggcc ccgcctcccg cccggccccg cctccctaac tcaccaggaa attcccttca    480
agccctggcc cgaactgagt ccccgcccac ccgccagcgt cacggcgccc gactcagctc    540
cgcgccggac ccacctccgc gccctcaggc cctgcatatg ccccgccccg cgcggaagtt    600
ccggcggttg gttgccttgc gcggccgtta cagcctttgc cctaagcctc gccccctttc    660
cccctgcctg cccaatcccg actgcttcct tgggtggggg cgtggctatg gggcgaggcg    720
ctctcaggtg gaggccgtgc cccgctccgc gctcacgaag ctgcgtcact tccggcgtgt    780
gcgtctggcg tccgcgcgct gcacaatggc ggctctgaag agttggctgt cgcgcagcgt    840
aacttcattc ttcaggtaca gacagtgttt gtgtgttcct gttgtggcta actttaagaa    900
gcggtgtttc tcagaattga taagaccatg gcacaaaact gtgacgattg ctttggagt     960 aaccctgtgt gcggttccta ttgcacagaa atcagagcct cattcccctta gtagtgaagc    1020 attgatgagg agagcagtgt ctttggtaac agatagcacc tctacctttc tctctcagac    1080
cacatatgcg ttgattgaag ctattactga atatactaag gctgtttata ccttaacttc    1140
tctttaccga caatatacaa gtttacttgg gaaaatgaat tcagaggagg aagatgaagt    1200
gtggcaggtg atcataggag ccagagctga gatgacttca aaacaccaag agtacttgaa    1260
```

-continued

| | |
|---|---|
| gctggaaacc acttggatga ctgcagttgg tctttcagag atggcagcag aagctgcata | 1320 |
| tcaaactggc gcagatcagg cctctataac cgccaggaat cacattcagc tggtgaaact | 1380 |
| gcaggtggaa gaggtgcacc agctctcccg aaaagcagaa accaagctgg cagaagcaca | 1440 |
| gatagaagag ctccgtcaga aaacacagga ggaaggggag gagcgggctg agtcggagca | 1500 |
| ggaggcctac ctgcgtgagg attgagggcc tgagcacact gccctgtctc cccactcagt | 1560 |
| ggggaaagca gggcagatg ccaccctgcc cagggttggc atgactgtct gtgcaccgag | 1620 |
| aagaggcggc agatcctgcc ctggccaatc aggcgagacg cctttgtgag ctgtgagtgc | 1680 |
| ctcctgtggt ctcaggcttg cgctggacct ggttcttagc ccttgggcac tgcaccctgt | 1740 |
| ttaacatttc accccactct gtacagctgc tcttacccat ttttttacc tcacacccaa | 1800 |
| agcatttgc ctacctgggt cagagagagg agtcctttt gtcatgccct taagttcagc | 1860 |
| aactgtttaa cctgttttca gtcttattta cgtcgtcaaa aatgatttag tacttgttcc | 1920 |
| ctctgttggg atgccagttg tggcagggg aggggaacct gtccagtttg tacgatttct | 1980 |
| ttgtatgtat ttctgatgtg ttctctgatc tgccccact gtcctgtgag acagctgag | 2040 |
| gccaaggagt gaaaaaccta ttactactaa gagaaggggt gcagagtgtt tacctggtgc | 2100 |
| tctcaacagg acttaacatc aacaggactt aacacaggcc tcttgttcct tcctttcttt | 2160 |
| ccgtttctct attgtatcca aaggagaaga gtgtaagatt ttgtttgcat ctgaaagaga | 2220 |
| aaatgcgtct ctcctggggt cctaaaaaaa aaaaaaaa aaaaa | 2265 |

<210> SEQ ID NO 12
<211> LENGTH: 3031
<212> TYPE: DNA
<213> ORGANISM: Homo sapiens

<400> SEQUENCE: 12

| | |
|---|---|
| caatcgcgaa accccgagga gcgctcgggc tgtctgcgga ccctgccgcg tgcaggggtc | 60 |
| gcggccggct ggagctggga gtgaggcggc ggaggagcca ggtgaggagg agccaggaag | 120 |
| gcagttggtg ggaagtccag cttgggtccc tgaggagctg tgagaaggag atgcggctgc | 180 |
| tgctggccct gttggggtc ctgctgagtg tgcctgggcc tccagtcttg tcctggagg | 240 |
| cctctgagga agtggagctt gagccctgcc tggctcccag cctggagcag caagagcagg | 300 |
| agctgacagt agcccttggg cagcctgtgc gtctgtgctg tgggcgggct gagcgtggtg | 360 |
| gccactggta caaggagggc agtcgcctgg cacctgctgg ccgtgtacgg ggctggaggg | 420 |
| gccgcctaga gattgccagc ttcctacctg aggatgctgg ccgctacctc tgcctggcac | 480 |
| gaggctccat gatcgtcctg cagaatctca ccttgattac aggtgactcc ttgacctcca | 540 |
| gcaacgatga tgaggacccc aagtcccata gggaccctc gaataggcac agttaccccc | 600 |
| agcaagcacc ctactggaca cacccccagc gcatggagaa gaaactgcat gcagtacctg | 660 |
| cggggaacac cgtcaagttc cgctgtccag ctgcaggcaa ccccacgccc accatccgct | 720 |
| ggcttaagga tggacaggcc tttcatgggg agaaccgcat tggaggcatt cggctgcgcc | 780 |
| atcagcactg gagtctcgtg atggagagcg tggtgccctc ggaccgcggc acatacacct | 840 |
| gcctggtaga aacgctgtg ggcagcatcc gctataacta cctgctagat gtgctggagc | 900 |
| ggtccccgca ccggcccatc ctgcaggccg ggctcccggc caacaccaca gccgtggtgg | 960 |
| gcagcgacgt ggagctgctg tgcaaggtgt acagcgatgc ccagcccac atccagtggc | 1020 |
| tgaagcacat cgtcatcaac ggcagcagct tcggagccga cggttttccc tatgtgcaag | 1080 |
| tcctaaagac tgcagacatc aatagctcag aggtggaggt cctgtacctg cggaacgtgt | 1140 |

```
cagccgagga cgcaggcgag tacacctgcc tcgcaggcaa ttccatcggc ctctcctacc    1200
agtctgcctg gctcacggtg ctgccagagg aggacccccac atggaccgca gcagcgcccg   1260
aggccaggta tacggacatc atcctgtacg cgtcgggctc cctggccttg gctgtgctcc    1320
tgctgctggc cgggctgtat cgagggcagg cgctccacgg ccggcacccc cgcccgcccg    1380
ccactgtgca gaagctctcc cgcttccctc tggcccgaca gttctccctg gagtcaggct    1440
cttccggcaa gtcaagctca tccctggtac gaggcgtgcg tctctcctcc agcggccccg    1500
ccttgctcgc cggcctcgtg agtctagatc tacctctcga cccactatgg gagttccccc    1560
gggacaggct ggtgcttggg aagcccctag gcgagggctg cttttggccag gtagtacgtg    1620 cagaggcctt tggcatggac cctgcccggc ctgaccaagc cagcactgtg gccgtcaaga    1680
tgctcaaaga caacgcctct gacaaggacc tggccgacct ggtctcggag atggaggtga    1740
tgaagctgat cggccgacac aagaacatca tcaacctgct tggtgtctgc acccaggaag    1800
ggcccctgta cgtgatcgtg gagtgcgccg ccaagggaaa cctgcgggag ttcctgcggg    1860
cccggcgccc cccaggcccc gacctcagcc ccgacggtcc tcggagcagt gagggccgc    1920 tctccttccc agtcctggtc tcctgcgcct accaggtggc ccgaggcatg cagtatctgg    1980
agtcccggaa gtgtatccac cgggacctgg ctgcccgcaa tgtgctggtg actgaggaca    2040
atgtgatgaa gattgctgac tttgggctgg cccgcgcgt ccaccacatt gactactata    2100
agaaaaccag caacggccgc ctgcctgtga gtggatggc gcccgaggcc ttgtttgacc    2160
gggtgtacac acaccagagt gacgtgtggt cttttgggat cctgctatgg gagatcttca    2220
ccctcggggg ctccccgtat cctggcatcc cggtggagga gctgttctcg ctgctgcggg    2280
agggacatcg gatggaccga cccccacact gcccccagaa gctgtacggg ctgatgcgtg    2340
agtgctggca cgcagcgccc tcccagaggc ctaccttcaa gcagctggtg gaggcgctgg    2400
acaaggtcct gctggccgtc tctgaggagt acctcgacct ccgcctgacc ttcggaccct    2460
attccccctc tggtggggac gccagcagca cctgctcctc cagcgattct gtcttcagcc    2520
acgaccccct gccattggga tccagctcct ccccttcgg gtctggggtg cagacatgag    2580
caaggctcaa ggctgtgcag gcacataggc tggtggcctt gggccttggg gctcagccac    2640
agcctgacac agtgctcgac cttgatagca tggggcccct ggcccagagt tgctgtgccg    2700
tgtccaaggg ccgtgccctt gcccttggag ctgccgtgcc tgtgtcctga tggcccaaat    2760
gtcagggttc tgctcggctt cttggaccaa ggcgcttagt ccccatcccg ggtttggctg    2820
agcctggctg gagagctgct atgctaaacc tcctgcctcc caataccagc aggaggttct    2880
gggcctctga acccccttc cccacacctc ccctgctgc tgctgcccca gcgtcttgac    2940
gggagcattg gccctgagc ccagagaagc tggaagcctg ccgaaaacag gagcaaatgg    3000
cgttttataa attattttt tgaaataaaa a                                    3031

<210> SEQ ID NO 13
<211> LENGTH: 2321
<212> TYPE: DNA
<213> ORGANISM: Homo sapiens

<400> SEQUENCE: 13
gtcctcaacc aagatggcgc ggatggcttc aggcgcatca cgacaccggc gcgtcacgcg     60
acccgcccta cgggcacctc ccgcgctttt cttagcgccg cagacggtgg ccgagcgggg    120
gaccgggaag catggcccgg gggtcggcgg ttgcctgggc ggcgctcggg ccgttgttgt    180
```

| | |
|---|---|
| ggggctgcgc gctgggctg cagggcggga tgctgtaccc ccaggagagc ccgtcgcggg | 240 |
| agtgcaagga gctggacggc ctctggagct tccgcgccga cttctctgac aaccgacgcc | 300 |
| ggggcttcga ggagcagtgg taccggcggc cgctgtggga gtcaggcccc accgtggaca | 360 |
| tgccagttcc ctccagcttc aatgacatca gccaggactg gcgtctgcgg cattttgtcg | 420 |
| gctgggtgtg gtacgaacgg gaggtgatcc tgccggagcg atggacccag gacctgcgca | 480 |
| caagagtggt gctgaggatt ggcagtgccc attcctatgc catcgtgtgg gtgaatgggg | 540 |
| tcgacacgct agagcatgag ggggctaccc tccccttcga ggccgacatc agcaacctgg | 600 |
| tccaggtggg gcccctgccc tcccggctcc gaatcactat cgccatcaac aacacactca | 660 |
| ccccaccac cctgccacca ggaccatcc aatacctgac tgacacctcc aagtatccca | 720 |
| agggttactt tgtccagaac acatattttg acttttcaa ctacgctgga ctgcagcggt | 780 |
| ctgtacttct gtacacgaca cccaccacct acatcgatga catcaccgtc accaccagcg | 840 |
| tggagcaaga cagtgggctg gtgaattacc agatctctgt caagggcagt aacctgttca | 900 |
| agttggaagt gcgtcttttg gatgcagaaa acaaagtcgt ggcgaatggg actgggaccc | 960 |
| agggccaact taaggtgcca ggtgtcagcc tctggtggcc gtacctgatg cacgaacgcc | 1020 |
| ctgcctatct gtattcattg gaggtgcagc tgactgcaca gacgtcactg gggcctgtgt | 1080 |
| ctgacttcta cacactccct gtggggatcc gcactgtggc tgtcaccaag agccagttcc | 1140 |
| tcatcaatgg gaaacctttc tatttccacg gtgtcaacaa gcatgaggat gcggacatcc | 1200 |
| gagggaaggg cttcgactgg ccgctgctgg tgaaggactt caacctgctt cgctggcttg | 1260 |
| gtgccaacgc tttccgtacc agccactacc cctatgcaga ggaagtgatg cagatgtgtg | 1320 |
| accgctatgg gattgtggtc atcgatgagt gtcccggcgt gggcctggcg ctgccgcagt | 1380 |
| tcttcaacaa cgtttctctg catcaccaca tgcaggtgat ggaagaagtg gtgcgtaggg | 1440 |
| acaagaacca ccccgcggtc gtgatgtggt ctgtggccaa cgagcctgcg tcccacctag | 1500 |
| aatctgctgg ctactacttg aagatggtga tcgctcacac caaatccttg gacccctccc | 1560 |
| ggcctgtgac ctttgtgagc aactctaact atgcagcaga caaggggggct ccgtatgtgg | 1620 |
| atgtgatctg tttgaacagc tactactctt ggtatcacga ctacgggcac ctggagttga | 1680 |
| ttcagctgca gctggccacc cagtttgaga actggtataa aagtatcag aagcccatta | 1740 |
| ttcagagcga gtatggagca gaaacgattg cagggtttca ccaggatcca cctctgatgt | 1800 |
| tcactgaaga gtaccagaaa agtctgctag agcagtacca tctgggtctg gatcaaaaac | 1860 |
| gcagaaaata cgtggttgga gagctcattt ggaattttgc cgatttcatg actgaacagt | 1920 |
| caccgacgag agtgctgggg aataaaaagg ggatcttcac tcggcagaga caaccaaaaa | 1980 |
| gtgcagcgtt ccttttgcga gagagatact ggaagattgc caatgaaacc aggtatcccc | 2040 |
| actcagtagc caagtcacaa tgtttggaaa acagcctgtt tacttgagca agactgatac | 2100 |
| cacctgcgtg tcccttcctc cccgagtcag ggcgacttcc acagcagcag aacaagtgcc | 2160 |
| tcctggactg ttcacggcag accagaacgt ttctggcctg ggttttgtgg tcatctattc | 2220 |
| tagcagggaa cactaaaggt ggaaataaaa gattttctat tatggaaata aagagttggc | 2280 |
| atgaaagtgg ctactgaaaa aaaaaaaaaa aaaaaaaaa a | 2321 |

<210> SEQ ID NO 14
<211> LENGTH: 1606
<212> TYPE: DNA
<213> ORGANISM: Homo sapiens

<400> SEQUENCE: 14

-continued

```
aaatgtgacc ggccgcggct ccggcagtca acgcctgcct cctctcgagc gtcctcagcg      60
cagccgccgc ccgcggagcc agcacgaacg agcccagcac cggccggatg gagcgtccgc     120
aacccgacag catgccccag gatttgtcag aggccctgaa ggaggccacc aaggaggtgc     180
acacccaggc agagaatgct gagttcatga ggaactttca aagggccag gtgacccgag      240 acggcttcaa gctggtgatg gcctccctgt accacatcta tgtggccctg gaggaggaga     300
ttgagcgcaa caaggagagc ccagtcttcg ccctgtcta cttcccagaa gagctgcacc      360
gcaaggctgc cctggagcag gacctggcct tctggtacgg ccccgctgg caggaggtca      420 tcccctacac accagccatg cagcgctatg tgaagcggct ccacgaggtg gggcgcacag     480
agcccgagct gctggtggcc cacgcctaca cccgctacct gggtgacctg tctggggcc     540 aggtgctcaa aaagattgcc cagaaagccc tggacctgcc cagctctggc gagggcctgg    600
ccttcttcac cttccccaac attgccagtg ccaccaagtt caagcagctc taccgctccc     660
gcatgaactc cctggagatg actcccgcag tcaggcagag ggtgatagaa gaggccaaga    720
ctgcgttcct gctcaacatc cagctctttg aggagttgca ggagctgctg acccatgaca    780
ccaaggacca gagcccctca cgggcaccag ggcttcgcca gcgggccagc aacaaagtgc     840
aagattctgc ccccgtggag actcccagag ggaagccccc actcaacacc cgctcccagg    900
ctccgcttct ccgatgggtc cttacactca gctttctggt ggcgacagtt gctgtagggc    960
tttatgccat gtgaatgcag gcatgctggc tcccagggcc atgaactttg tccggtggaa   1020
ggccttcttt ctagagaggg aattctcttg gctggcttcc ttaccgtggg cactgaaggc    1080
tttcagggcc tccagccctc tcactgtgtc cctctctctg gaaaggagga aggagcctat    1140
ggcatcttcc ccaacgaaaa gcacatccag gcaatggcct aaacttcaga gggggcgaag   1200
ggatcagccc tgcccttcag catcctcagt tcctgcagca gagcctggaa gacaccctaa    1260
tgtggcagct gtctcaaacc tccaaaagcc ctgagtttca agtatccttg ttgacacggc    1320
catgaccact ttccccgtgg gccatggcaa tttttacaca aacctgaaaa gatgttgtgt    1380
cttgtgtttt tgtcttattt ttgttggagc cactctgttc ctggctcagc ctcaaatgca    1440 gtattttgt tgtgttctgt tgtttttata gcagggttgg ggtggttttt gagccatgcg     1500
tgggtgggga gggaggtgtt taacggcact gtggccttgg tctaactttt gtgtgaaata    1560
ataaacaaca ttgtctgata gtagcttgaa aaaaaaaaa aaaaaa                    1606
```

<210> SEQ ID NO 15
<211> LENGTH: 3879
<212> TYPE: DNA
<213> ORGANISM: Homo sapiens

<400> SEQUENCE: 15

```
atcagacgcg cagaggaggc ggggccgcgg ctggtttcct gccgggggc ggctctgggc      60 cgccgagtcc cctcctcccg ccctgagga ggaggagccg ccgccacccg ccgcgcccga     120
cacccgggag gccccgccag cccgcgggag aggcccagcg ggagtcgcgg aacagcaggc    180
ccgagcccac cgcgccgggc cccggacgcc gcgcggaaaa gatgaattta caaccaattt    240
tctggattgg actgatcagt tcagtttgct gtgtgtttgc tcaaacagat gaaaatagat     300
gtttaaaagc aaatgccaaa tcatgtggag aatgtataca agcagggcca aattgtgggt    360
ggtgcacaaa ttcaacattt ttacaggaag gaatgcctac ttctgcacga tgtgatgatt    420
tagaagcctt aaaaaagaag ggttgccctc cagatgacat agaaaatccc agaggctcca   480
```

-continued

| | | |
|---|---|---|
| aagatataaa gaaaaataaa aatgtaacca accgtagcaa aggaacagca gagaagctca | 540 | |
| agccagagga tattactcag atccaaccac agcagttggt tttgcgatta agatcagggg | 600 | |
| agccacagac atttacatta aaattcaaga gagctgaaga ctatcccatt gacctctact | 660 | |
| accttatgga cctgtcttac tcaatgaaag acgatttgga gaatgtaaaa agtcttggaa | 720 | |
| cagatctgat gaatgaaatg aggaggatta cttcggactt cagaattgga tttggctcat | 780 | |
| ttgtggaaaa gactgtgatg ccttacatta gcacaacacc agctaagctc aggaaccctt | 840 | |
| gcacaagtga acagaactgc accagcccat ttagctacaa aaatgtgctc agtcttacta | 900 | |
| ataaaggaga agtatttaat gaacttgttg gaaaacagcg catatctgga aatttggatt | 960 | |
| ctccagaagg tggtttcgat gccatcatgc aagttgcagt tgtggatca ctgattggct | 1020 | |
| ggaggaatgt tacacggctg ctggtgtttt ccacagatgc cgggtttcac tttgctggag | 1080 | |
| atgggaaact tggtggcatt gttttaccaa atgatggaca atgtcacctg gaaaataata | 1140 | |
| tgtacacaat gagccattat tatgattatc cttctattgc tcaccttgtc cagaaactga | 1200 | |
| gtgaaaataa tattcagaca attttgcag ttactgaaga atttcagcct gtttacaagg | 1260 | |
| agctgaaaaa cttgatccct aagtcagcag taggaacatt atctgcaaat tctagcaatg | 1320 | |
| taattcagtt gatcattgat gcatacaatt ccctttcctc agaagtcatt ttggaaaacg | 1380 | |
| gcaaattgtc agaaggcgta acaataagtt acaaatctta ctgcaagaac ggggtgaatg | 1440 | |
| gaacagggga aaatgaaga aaatgttcca atatttccat ggagatgag gttcaatttg | 1500 | |
| aaattagcat aacttcaaat aagtgtccaa aaaaggattc tgacagcttt aaaattaggc | 1560 | |
| ctctgggctt tacggaggaa gtagaggtta ttcttcagta catctgtgaa tgtgaatgcc | 1620 | |
| aaagcgaagg catccctgaa agtcccaagt gtcatgaagg aaatgggaca tttgagtgtg | 1680 | |
| gcgcgtgcag gtgcaatgaa gggcgtgttg gtagacattg tgaatgcagc acagatgaag | 1740 | |
| ttaacagtga agacatggat gcttactgca ggaaagaaaa cagttcagaa atctgcagta | 1800 | |
| acaatggaga gtgcgtctgc ggacagtgtg tttgtaggaa gagggataat acaaatgaaa | 1860 | |
| tttattctgg caaattctgc gagtgtgata atttcaactg tgatagatcc aatggcttaa | 1920 | |
| tttgtggagg aaatggtgtt tgcaagtgtc gtgtgtgtga gtgcaacccc aactacactg | 1980 | |
| gcagtgcatg tgactgttct ttggatacta gtacttgtga agccagcaac ggacagatct | 2040 | |
| gcaatggccg gggcatctgc gagtgtggtg tctgtaagtg tacagatccg aagtttcaag | 2100 | |
| ggcaaacgtg tgagatgtgt cagacctgcc ttggtgtctg tgctgagcat aaagaatgtg | 2160 | |
| ttcagtgcag agccttcaat aaaggagaaa agaaagacac atgcacacag gaatgttcct | 2220 | |
| attttaacat taccaaggta gaaagtcggg acaaattacc ccagccggtc caacctgatc | 2280 | |
| ctgtgtccca ttgtaaggag aaggatgttg acgactgttg gttctatttt acgtattcag | 2340 | |
| tgaatgggaa caacgaggtc atggttcatg ttgtggagaa tccagagtgt cccactggtc | 2400 | |
| cagacatcat tccaattgta gctggtgtgg ttgctggaat tgttcttatt ggccttgcat | 2460 | |
| tactgctgat atggaagctt ttaatgataa ttcatgacag aagggagttt gctaaatttg | 2520 | |
| aaaaggagaa aatgaatgcc aaatgggaca cgggtgaaaa tcctatttat aagagtgccg | 2580 | |
| taacaactgt ggtcaatccg aagtatgagg gaaaatgagt actgcccgtg caaatcccac | 2640 | |
| aacactgaat gcaaagtagc aatttccata gtcacagtta ggtagcttta gggcaatatt | 2700 | |
| gccatggttt tactcatgtg caggttttga aaatgtacaa tatgtataat ttttaaaatg | 2760 | |
| ttttattatt ttgaaaataa tgttgtaatt catgccaggg actgacaaaa gacttgagac | 2820 | |
| aggatggtta ctcttgtcag ctaaggtcac attgtgcctt tttgacccttt tcttcctgga | 2880 | |

-continued

```
ctattgaaat caagcttatt ggattaagtg atatttctat agcgattgaa agggcaatag    2940
ttaaagtaat gagcatgatg agagtttctg ttaatcatgt attaaaactg attttttagct   3000 ttacaaatat gtcagtttgc agttatgcag aatccaaagt aaatgtcctg ctagctagtt    3060
aaggattgtt ttaaatctgt tattttgcta tttgcctgtt agacatgact gatgacatat    3120
ctgaaagaca agtatgttga gagttgctgg tgtaaaatac gtttgaaata gttgatctac    3180
aaaggccatg ggaaaaattc agagagttag gaaggaaaaa ccaatagctt taaaacctgt    3240
gtgccatttt aagagttact taatgtttgg taactttta t gccttcactt tacaaattca    3300
agccttagat aaaagaaccg agcaattttc tgctaaaaag tccttgattt agcactattt    3360
acatacaggc catactttac aaagtatttg ctgaatgggg accttttgag ttgaatttat    3420
tttattattt ttattttgtt taatgtctgg tgcttt ctgt cacctcttct aatcttttaa    3480
tgtatttgtt tgcaattttg gggtaagact tttttttatga gtactttttc tttgaagttt    3540
tagcggtcaa tttgcctttt taatgaacat gtgaagttat actgtggcta tgcaacagct    3600
ctcacctacg cgagtcttac tttgagttag tgccataaca gaccactgta tgtttacttc    3660
tcaccatttg agttgcccat cttgtttcac actagtcaca ttcttgtttt aagtgccttt    3720
agttttaaca gttcacttt tacagtgcta tttactgaag ttatttatta aatatgccta    3780
aaatacttaa atcggatgtc ttgactctga tgtattttat caggttgtgt gcatgaaatt    3840
tttatagatt aagaagttg aggaaaagca aaaaaaaaa                            3879
```

<210> SEQ ID NO 16
<211> LENGTH: 3751
<212> TYPE: DNA
<213> ORGANISM: Homo sapiens

<400> SEQUENCE: 16

```
cgggcgcagc agctggaacg ggagtactgc gacgcggccc ggagtcggcc ttgtagggc     60 gaaggtgcag ggagatcgcg gcgggcgcag tcttgagcgc cggagcgcgt ccctgccctt    120
agcggggctt gccccagtcg caggggcaca tccagccgct gcggctgaca gcagccgcgc    180
gcgcgggagt ctgcggggtc gcggcagccg cacctgcgcg ggcgaccagc gcaaggtccc    240
cgcccggctg ggcgggcagc aagggccggg gagagggtgc gggtgcaggc gggggcccca    300
cagggccacc ttcttgcccg gcggctgccg ctggaaaatg tctcaggaga ggcccacgtt    360
ctaccggcag gagctgaaca agacaatctg ggaggtgccc gagcgttacc agaacctgtc    420
tccagtgggc tctggcgcct atggctctgt gtgtgctgct tttgacacaa aaacggggtt    480
acgtgtggca gtgaagaagc tctccagacc atttcagtcc atcattcatg cgaaaagaac    540
ctacagagaa ctgcggttac ttaaacatat gaaacatgaa aatgtgattg gtctgttgga    600 cgttttttaca cctgcaaggt ctctggagga attcaatgat gtgtatctgg tgacccatct    660
catgggggca gatctgaaca acattgtgaa atgtcagaag cttacagatg accatgttca    720
gttccttatc taccaaattc tccgaggtct aaagtatata cattcagctg acataattca    780
cagggaccta aaacctagta atctagctgt gaatgaagac tgtgagctga agattctgga    840
ttttggactg gctcggcaca cagatgatga aatgacaggc tacgtggcca ctaggtggta    900
cagggctcct gagatcatgc tgaactggat gcattacaac cagacagttg atatttggtc    960
agtgggatgc ataatggccg agctgttgac tggaagaaca ttgttcctg gtacagacca   1020 tattgatcag ttgaagctca ttttaagact cgttggaacc ccaggggctg agcttttgaa    1080
```

```
gaaaatctcc tcagagtctg caagaaacta tattcagtct ttgactcaga tgccgaagat    1140
gaactttgcg aatgtattta ttggtgccaa tcccctggct gtcgacttgc tggagaagat    1200
gcttgtattg gactcagata agagaattac agcggcccaa gcccttgcac atgcctactt    1260
tgctcagtac cacgatcctg atgatgaacc agtggccgat ccttatgatc agtcctttga    1320
aagcagggac ctccttatag atgagtggaa aagcctgacc tatgatgaag tcatcagctt    1380
tgtgccacca ccccttgacc aagaagagat ggagtcctga gcacctggtt tctgttctgt    1440
tgatcccact tcactgtgag gggaaggcct tttcatggga actctccaaa tattattcaa    1500
gtgcctcttg ttgcagagat ttcctccatg gtggaagggg gtgtgcgtgc gtgtgcgtgc    1560
gtgttagtgt gtgtgcatgt gtgtgtctgt ctttgtggga gggtaagaca atatgaacaa    1620
actatgatca cagtgacttt acaggaggtt gtggatgctc cagggcagcc tccaccttgc    1680
tcttctttct gagagttggc tcaggcagac aagagctgct gtccttttag gaatatgttc    1740
aatgcaaagt aaaaaaatat gaattgtccc caatcccggt catgcttttg ccactttggc    1800
ttctcctgtg accccacctt gacggtgggg cgtagacttg acaacatccc acagtggcac    1860
ggagagaagg cccatacctt ctggttgctt cagacctgac accgtccctc agtgatacgt    1920
acagccaaaa aggaccaact ggcttctgtg cactagcctg tgattaactt gcttagtatg    1980
gttctcagat cttgacagta tatttgaaac tgtaaatatg tttgtgcctt aaaaggagag    2040
aagaaagtgt agatagttaa aagactgcag ctgctgaagt tctgagccgg gcaagtcgag    2100
agggctgttg gacagctgct tgtgggcccg gagtaatcag gcagccttca taggcggtca    2160
tgtgtgcatg tgagcacatg cgtatatgtg cgtctctctt tctccctcac ccccaggtgt    2220
tgccatttct ctgcttaccc ttcacctttg gtgcagaggt tcttgaaata tctgccccag    2280
tagtcagaag caggttcttg atgtcatgta cttcctgtgt actctttatt tctagcagag    2340
tgaggatgtg ttttgcacgt cttgctattt gagcatgcac agctgcttgt cctgctctct    2400
tcaggaggcc ctggtgtcag gcaggtttgc cagtgaagac ttcttgggta gtttagatcc    2460
catgtcacct cagctgatat tatggcaagt gatatcacct ctcttcagcc cctagtgcta    2520
ttctgtgttg aacacaattg atacttcagg tgcttttgat gtgaaaatca tgaaagagg     2580 aacaggtgga tgtatagcat ttttattcat gccatctgtt ttcaaccaac tattttgag    2640 gaattatcat gggaaaagac cagggctttt cccaggaata tcccaaactt cggaaacaag    2700
ttattctctt cactcccaat aactaatgct aagaaatgct gaaaatcaaa gtaaaaaatt    2760
aaagcccata aggccagaaa ctccttttgc tgtctttctc taaatatgat tacttttaaaa   2820 taaaaagta acaaggtgtc ttttccactc ctatggaaaa gggtcttctt ggcagcttaa     2880
cattgacttc ttggtttggg gagaaataaa ttttgtttca gaattttgta tattgtagga    2940 atccctttgag aatgtgattc cttttgatgg ggagaaaggg caaattattt taatatttg    3000 tatttcaac tttataaaga taaaatatcc tcagggtgg agaagtgtcg ttttcataac     3060
ttgctgaatt tcaggcattt tgttctacat gaggactcat atatttaagc cttttgtgta    3120
ataagaaagt ataaagtcac ttccagtgtt ggctgtatga cagaatcttg tatttgggcc    3180
aaggtgtttc catttctcaa tcagtgcagt gatacatgta ctccagaggg acagggtgga    3240 cccctgagt caactggagc aagaaggaag gaggcagact gatggcgatt ccctctcacc    3300
cgggactctc cccctttcaa ggaaagtgaa ccttttaaagt aaaggcctca tctcctttat    3360
tgcagttcaa atcctcacca tccacagcaa gatgaatttt atcagccatg tttggttgta    3420
aatgctcgtg tgatttccta cagaaatact gctctgaata ttttgtaata aaggtctttg    3480
```

```
cacatgtgac cacatacgtg ttaggaggct gcatgctctg gaagcctgga ctctaagctg    3540
gagctcttgg aagagctctt cggtttctga gcataatgct cccatctcct gatttctctg    3600
aacagaaaac aaaagagaga atgagggaaa ttgctatttt atttgtattc atgaacttgg    3660
ctgtaatcag ttatgccgta taggatgtca gacaatacca ctggttaaaa taaagcctat    3720
ttttcaaaaa aaaaaaaaaa aaaaaaaaa a                                    3751

<210> SEQ ID NO 17
<211> LENGTH: 3171
<212> TYPE: DNA
<213> ORGANISM: Homo sapiens

<400> SEQUENCE: 17
gggtgtgtgt gtgagtgaga gagcgagtga gtgagtgagt gagtgtgtgt gtgggggggga     60 ctcggcttgt tgttgtcggt gacttccccc tcccttcac cccttcccct cccgccgcc      120 gctgcagtgg ccgctccctg ggccgtagga atgagcgat aacgatgaca tcgaggtgga    180
gagcgacgaa gagcaacaga ggtttcaatc tgcggctgac aaacgggctc atcataatgc    240
actggaacga aaacgtaggg accacatcaa agacagcttt cacagtttgc gggactcagt    300
cccatcactc caaggagaga aggcatcccg ggcccaaatc ctagacaaag ccacagaata    360
tatccagtat atgcgaagga aaaccacac acaccagcaa gatattgacg acctcaagcg    420
gcagaatgct cttctggagc agcaaggtga gcacccgagc tcgtgggca gctggccctg    480 ctgtgctcca gccaggtcag gctttggcac ctgggcctgc agagtcagag ccagtcatgg    540
agtatgtgct cagtagcagg cttggtcctg cttcttgggg cctgagtaac tgagtgttag    600
agccgtcctg aggaaggacc tgaggcgcca gtgaggagac agtggaagct aggaagttgg    660
acatctggag acttgtatct tttctggcct gacctctccc gttcttgggt ctcaggtgct    720
ctgcctgcag tagggatcac acctggcatc aggtgtctga aaagagctttt gaggtccttg    780 gagtggaatg tgctgtgtaa gtaccagaga ctccaggtgt tcagggacag tgagccctcc    840
ccattgtcaa tggtagtcca atcagggcag cctatgggct aggcccatgc tgttctcaat    900
gctcacaccc gccttttcct acaaccacag gggaaagcga gagctgatca agttctttgt    960
tcctggggaa ttcacttctc ttcctccctc atggaagatg caagtaaaag gaaatgcaag   1020
taaccacctg ggttagaaaa cctcaaataa aataaaataa aataaattaa atgggttgac   1080
cttccaggct caagctgagc tgaaccaagg gatgggcagt gggtggtgtc agtgggttgg   1140
ttactgggcc aggcagcctg catgtagggg ctatttgaaa agcccaggta ttttatgtgt   1200
attggtgact tgcttccaag tgtccagctt gtcattccaa gtggatcttg tacacgagag   1260
ctaagccaaa actgttcttt ggctgatacg tcttatgtca tcctttcctg ctgttgtgtg   1320
gcctcacacc ttgtggagcc tcatgctcct gggccagctt ctcctctgtt attgcactgc   1380
tgaatcccac agggagctca cgctccagtc tctccacggg gcttccacgg caggacggtg   1440
acatcacaag ccttctcttc agagttgggt gggattgcag agtgtctgct ggctcccagg   1500
tccagctggg aaaggcggga gggaaatgaa gtgtgtgagt gaacagccac ccgaagggag   1560
ctacttctga gcatcttgag cctcggggc caacaagcaa gccttagga agaacaggct   1620 ggaccctgag tctgagactc ggttactccc caagtctcca gaaggcagta acacactccc   1680
ttggttgcct tttagtccgt gcactggaga aggcgaggtc aagtgcccaa ctgcagacca   1740 actaccccctc ctcagacaac agcctctaca ccaacgccaa gggcagcacc atctctgcct   1800
```

```
tcgatggggg ctcggactcc agctcggagt ctgagcctga agagcccaa agcaggaaga    1860 agctccggat ggaggccagc taagccactc ggggcaggcc agcaataaaa actgtctgtc    1920
tccatcgtct catcctcctt tcagttcgtt ggtagagccc tcagaaccat ttaaaagact    1980 ctttatttt ctctttctcc cttttttttt taaattttta ttttttacgta gaagctcttg    2040 gacaacagct ctcgttctcc ttccccattt ccactgtata ttttttaatg tattcccttc    2100
agggattccc tgtccccaac aggaattttt aaaccaaaac accccaactt ggcagctttt    2160
tctgtggagg acagacggcc ggccggacct ctgagcacat agtgtcctgc ccaccctacc    2220
agctcctcca gccctgccag gcacatgccc ggggacgcc tgccctgccc aggtggcctc    2280
ctggcctgcc ctcacctctg atagactttg tgaatctgaa ctgctctact ttgagaagat    2340
gaccggtttg gagtaatcag aatgaaccct cctccttttt aagggttttt ttttttttcct    2400 ttttctaaaa agctatgtat cgctcctatt gaaagaccag atccttaaag aagtttgtgg    2460
tataaaaaga aagtggggac agattcgcag cacagagtcg ctggcatgtt tcactcctgc    2520
ttctctcagc cagctgttta gcctgcggc gccagcctca cggagggccg tgtgacactc    2580
tcgtggtatg tatgggagac ggcagcagtg aagcagcagc caccagggag tggccatttg    2640 ggggttgggac agggagggtg ttttgggtgg catagaggtt ttgtattgag ggccagtgat    2700
gatgttttga tatttatttc ctgctactta aatttgaatc tgagtgaatt gtacctattt    2760
ctgatgatgt cggtcttgca aagcgacaga ttcataaagt aatgatgaaa tctttctttc    2820
ttcccgtgtg tatttctaag aaatagagcc aactgatttt gtatgtaaat accaagagca    2880
atttacctgg tactaaaccc gcaccccagt gcggacccctt cccagccctc atcccacttc    2940
ctttcctact gtcctggaac ctgtctccat tgtgtgatcc agccctggtt ctggctgtgg    3000
tcagcagatc ccagtgaagg gttttgtgtg tttaggcctc atttctttgt cttttttccta    3060 ctccgttcct ggcatttgct gatttctagt gtatactctg tagtcagttc gtgtttgatt    3120
ccattccatg gaaataaaaa gtatgttgta catacaaaaa aaaaaaaaaa a    3171
```

<210> SEQ ID NO 18
<211> LENGTH: 3065
<212> TYPE: DNA
<213> ORGANISM: Homo sapiens

<400> SEQUENCE: 18

```
ctcaggcggt ggctggaggc tgcgcatctg ggctttaaa catacaaagg gattgccagg      60
acctgcggcg gcggcggcgg cggcggggc tggggcgcgg gggccggacc atgagccgct     120
gagccgggca accccaggc caccgagcca gcggacccct ggagcgcagc cctgcgccgc     180
ggagcaggct ccaaccaggc ggcgacgcgg ccacacgcac cgagccagcg accccccggg     240
gacgcgcggg gccagggagc gctacgatgg aggcgctaat ggcccggggc gcgctcacgg     300 gtccctgag ggcgctctgt ctcctgggct gcctgctgag ccacgccgcc gccgcgccgt     360
cgcccatcat caagttcccc ggcgatgtcg ccccaaaac ggacaaagag ttggcagtgc     420
aatacctgaa caccttctat ggctgcccca aggagagctg caacctgttt gtgctgaagg     480
acacactaaa gaagatgcag aagttctttg gactgccca gacaggtgat cttgaccaga     540
ataccatcga ccatgcgg aagccacgct gcggcaaccc agatgtggcc aactacaact     600
tcttccctcg caagcccaag tgggacaaga accagatcac atacaggatc attggctaca     660
cacctgatct ggacccagag acagtggatg atgcctttgc tcgtgccttc caagtctgga     720
gcgatgtgac cccactgcgg ttttctcgaa tccatgatgg agaggcagac atcatgatca     780
```

```
actttggccg ctgggagcat ggcgatggat accccttttga cggtaaggac ggactcctgg    840
ctcatgcctt cgccccaggc actggtgttg ggggagactc ccattttgat gacgatgagc    900
tatggacctt gggagaaggc caagtggtcc gtgtgaagta tggcaacgcc gatgggagt     960 actgcaagtt ccccttcttg ttcaatggca aggagtacaa cagctgcact gataccggcc   1020
gcagcgatgg cttcctctgg tgctccacca cctacaactt tgagaaggat ggcaagtacg   1080
gcttctgtcc ccatgaagcc ctgttccacca tgggcggcaa cgctgaagga cagccctgca   1140
agtttccatt ccgcttccag ggcacatcct atgacagctg caccactgag gccgcacgg    1200 atggctaccg ctggtgcggc accactgagg actacgaccg cgacaagaag tatggcttct   1260
gccctgagac cgccatgtcc actgttggtg ggaactcaga aggtgccccc tgtgtcttcc   1320
ccttcacttt cctgggcaac aaatatgaga gctgcaccag cgccggccgc agtgacggaa   1380
agatgtggtg tgcgaccaca gccaactacg atgacgaccg caagtggggc ttctgccctg   1440
accaagggta cagcctgttc ctcgtggcag cccacgagtt tggccacgcc atggggctgg   1500
agcactccca agaccctggg gccctgatgg cacccattta cacctacacc aagaacttcc   1560
gtctgtccca ggatgacatc aagggcattc aggagctcta tggggcctct cctgacattg   1620
accttggcac cggcccccacc cccacactgg gccctgtcac tcctgagatc tgcaaacagg   1680
acattgtatt tgatgcatc gctcagatcc gtggtgagat cttcttcttc aaggaccggt    1740
tcatttggcg gactgtgacg ccacgtgaca agcccatggg gcccctgctg gtggccacat   1800
tctggcctga gctcccggaa aagattgatg cggtatacga ggccccacag gaggagaagg   1860
ctgtgttctt tgcagggaat gaatactgga tctactcagc cagcaccctg gagcgagggt   1920
accccaagcc actgaccagc ctgggactgc cccctgatgt ccagcgagtg gatgccgcct   1980
ttaactggag caaaaacaag aagacataca tctttgctgg agacaaattc tggagataca   2040
atgaggtgaa gaagaaaatg gatcctggct ttcccaagct catcgcagat gcctggaatg   2100
ccatccccga taacctggat gccgtcgtgg acctgcaggg cggcggtcac agctacttct   2160
tcaagggtgc ctattacctg aagctggaga ccaaagtctc gaagagcgtg aagtttggaa   2220
gcatcaaatc cgactggcta ggctgctgag ctggccctgg ctcccacagg cccttcctct   2280
ccactgcctt cgatacaccg ggcctggaga actagagaag gacccggagg ggcctggcag   2340
ccgtgccttc agctctacag ctaatcagca ttctcactcc tacctggtaa tttaagattc   2400
cagagagtgg ctcctcccgg tgcccaagaa tagatgctga ctgtactcct cccaggcgcc   2460
ccttccccct ccaatcccac caaccctcag agccaccccct aaagagatcc tttgatattt   2520
tcaacgcagc cctgctttgg gctgccctgg tgctgccaca cttcaggctc ttctccttttc   2580 acaaccttct gtggctcaca gaaccctttgg agccaatgga gactgtctca agagggcact   2640
ggtggcccga cagcctggca cagggcagtg ggacagggca tggccaggtg gccactccag   2700 accccctggct tttcactgct ggctgcctta gaaccttttct tacattagca gtttgctttg   2760
tatgcacttt gttttttttct ttgggtcttg ttttttttttt ccacttagaa attgcatttc   2820
ctgacagaag gactcaggtt gtctgaagtc actgcacagt gcatctcagc ccacatagtg   2880
atggttcccc tgttcactct acttagcatg tccctaccga gtctcttctc cactggatgg   2940
aggaaaacca agccgtggct tcccgctcag ccctccctgc ccctcccttc aaccattccc   3000
catgggaaat gtcaacaagt atgaataaag acacctactg agtgaaaaaa aaaaaaaaa    3060 aaaaa                                                                3065
```

<210> SEQ ID NO 19
<211> LENGTH: 4093
<212> TYPE: DNA
<213> ORGANISM: Homo sapiens

<400> SEQUENCE: 19

```
gtgagagagt gagcgagaca gaaagagaga gaagtgcacc agcgagccgg ggcaggaaga      60
ggaggttttcg ccaccggagc ggcccggcga cgcgctgaca gcttcccctg cccttcccgt    120
cggtcgggcc gccagccgcc gcagccctcg gcctgcacgc agccaccggc cccgctcccg    180
gagcccagcg ccgccgaggc cgcagccgcc cggccagtaa ggcggcgccg ccgcccggcc    240
accgcgcgcc ctgcgcttcc ctccgcccgc gctgcggcca tggcgcggcg ctgactggcc    300
tggcccggcc ccgccgcgct cccgctcgcc ccgacccgca ctcgggcccg cccgggctcc    360
ggcctgccgc cgcctcttcc ttctccagcc ggcaggcccg cgccgcttag gagggagagc    420
ccacccgcgc caggaggccg aacgcggact cgccacccgg cttcagaatg cagaagatg     480
atccatattt gggaaggcct gaacaaatgt ttcatttgga tccttctttg actcatacaa    540
tatttaatcc agaagtattt caaccacaga tggcactgcc aacagcagat ggcccatacc    600
ttcaaatatt agagcaacct aaacagagag gatttcgttt ccgttatgta tgtgaaggcc    660
catcccatgg tggactacct ggtgcctcta gtgaaaagaa caagaagtct taccctcagg    720
tcaaaatctg caactatgtg ggaccagcaa aggttattgt tcagttggtc acaaatggaa    780
aaaatatcca cctgcatgcc acagcctggg tgggaaaaca ctgtgaggat gggatctgca    840
ctgtaactgc tggacccaag gacatggtgg tcggcttcgc aaacctgggt atacttcatg    900
tgacaaagaa aaaagtattt gaaacactgg aagcacgaat gacagaggcg tgtataaggg    960
gctataatcc tggactcttg gtgcaccctg accttgccta tttgcaagca gaaggtggag   1020
gggaccggca gctgggagat cgggaaaaag agctaatccg ccaagcagct ctgcagcaga   1080
ccaaggagat ggacctcagc gtggtgcggc tcatgtttac agcttttctt ccggatagca   1140
ctggcagctt cacaaggcgc ctggaacccg tggtatcaga cgccatctat gacagtaaag   1200
cccccaatgc atccaacttg aaaattgtaa gaatggacag gacagctgga tgtgtgactg   1260
gaggggagga aatttatctt ctttgtgaca agttcagaa agatgacatc cagattcgat    1320
tttatgaaga ggaagaaaat ggtggagtct gggaaggatt tggagatttt tcccccacag   1380
atgttcatag acaatttgcc attgtcttca aaactccaaa gtataaagat attaatatta   1440
caaaaccagc ctctgtgttt gtccagcttc ggaggaaatc tgacttggaa actagtgaac   1500
caaaaccttt cctctactat cctgaaatca agataaaga agaagtgcag aggaaacgtc   1560
agaagctcat gcccaatttt tcggatagtt tcggcggtgg tagtggtgct ggagctggag   1620
gcggaggcat gtttggtagt ggcggtggag gagggggcac tggaagtaca ggtccagggt   1680
atagcttccc acactatgga tttcctactt atggtgggat tactttccat cctgaactg    1740
ctaaatctaa tgctgggatg aagcatggaa ccatggacac tgaatctaaa aaggaccctg   1800
aaggttgtga caaaagtgat gacaaaaaca ctgtaaaccct ctttgggaaa gttattgaaa   1860
ccacagagca agatcaggag cccagcgagg ccaccgttgg gaatggtgag gtcactctaa   1920
cgtatgcaac aggaacaaaa gaagagagtg ctggagttca ggataacctc tttctagaga   1980
aggctatgca gcttgcaaag aggcatgcca tgcccttttt cgactacgcg gtgacaggag   2040
acgtgaagat gctgctggcc gtccagcgcc atctcactgc tgtgcaggat gagaatgggg   2100
acagtgtctt acacttagca atcatccacc ttcattctca acttgtgagg gatctactag   2160
```

```
aagtcacatc tggtttgatt tctgatgaca ttatcaacat gagaaatgat ctgtaccaga      2220
cgcccttgca cttggcagtg atcactaagc aggaagatgt ggtggaggat ttgctgaggg      2280
ctggggccga cctgagcctt ctggaccgct tgggtaactc tgttttgcac ctagctgcca      2340
aagaaggaca tgataaagtt ctcagtatct tactcaagca caaaaaggca gcactacttc      2400
ttgaccaccc caacggggac ggtctgaatg ccattcatct agccatgatg agcaatagcc      2460
tgccatgttt gctgctgctg gtggccgctg ggctgacgc caatgctcag gagcagaagt      2520
ccgggcgcac agcactgcac ctggctgtgg agcacgacaa catctcattg gcaggctgcc      2580
tgctcctgga gggtgatgcc catgtggaca gtactaccta cgatggaacc acaccctgc      2640 atatagcagc tgggagaggg tccaccaggc tggcagctct tctcaaagca gcaggagcag      2700 atccctggt ggagaacttt gagcctctct atgacctgga tgactcttgg gaaaatgcag      2760
gagaggatga aggagttgtg cctggaacca cgcctctaga tatggccacc agctggcagg      2820
tatttgacat attaaatggg aaaccatatg agccagagtt tacatctgat gatttactag      2880
cacaaggaga catgaaacag ctggctgaag atgtgaagct gcagctgtat aagttactag      2940
aaattcctga tccagacaaa aactgggcta ctctggcgca gaaattaggt ctggggatac      3000
ttaataatgc cttccggctg agtcctgctc cttccaaaac acttatggac aactatgagg      3060
tctctggggg tacagtcaga gagctggtgg aggccctgag acaaatgggc tacaccgaag      3120
caattgaagt gatccaggca gcctccagcc cagtgaagac cacctctcag gcccactcgc      3180
tgcctctctc gcctgcctcc acaaggcagc aaatagacga gctccgagac agtgacagtg      3240
tctgcgacag cggcgtggag acatccttcc gcaaactcag cttaccgag tctctgacca      3300 gtggtgcctc actgctaact ctcaacaaaa tgccccatga ttatgggcag gaaggacctc      3360
tagaaggcaa aatttagcct gctgacaatt tcccacaccg tgtaaaccaa agccctaaaa      3420
ttccactgcg ttgtccacaa gacagaagct gaagtgcatc caaaggtgct cagagagccg      3480
gcccgcctga atcattctcg atttaactcg agaccttttc aacttggctt cctttcttgg      3540
ttcataaatg aattttagtt tggttcactt acagatagta tctagcaatc acaaacactgg      3600 ctgagcggat gcatctgggg atgaggttgc ttactaagct ttgccagctg ctgctggatc      3660
acagctgctt tctgttgtca ttgctgttgt ccctctgcta cgttcctatt gtcattaaag      3720
gtatcacggt cgccacctgg cattccttct gaccacagca tcattttgca ttcaaattaa      3780
gggttaagaa aagagatatt ttaaaatgag agtcacttga tgtgccattt taaaaaaaaa      3840
ggcatattgc tttttctaat gtggttattt ctctgatttg caaaaaaaaa aaaaaaaaaa      3900
atacttgtca atatttaaac atggttacaa tcattgctga aaatggtatt ttcccccttt      3960 tctgcattt gctattgtaa atatgttttt tagatcaaat actttaaagg aaaaaatgtt      4020
ggatttataa atgctatttt ttatttttact tttataataa aaggaaaagc aaattgatga      4080
cctcaaaaaa aaa                                                        4093

<210> SEQ ID NO 20
<211> LENGTH: 925
<212> TYPE: DNA
<213> ORGANISM: Homo sapiens

<400> SEQUENCE: 20
agtctgggac gcgccgccgc catgatcatc cctgtacgct gcttcacttg tggcaagatc       60
gtcggcaaca agtgggaggc ttacctgggg ctgctgcagg ccgagtacac cgaggggat      120
```

```
gcgctggatg ccctgggcct gaagcgctac tgctgccgcc ggatgctgct ggcccacgtg    180
gacctgatcg agaagctgct caattatgca cccctggaga agtgaccacg ctggaaccca    240
cccacccgct gtgctgacca tgggccctga gcgtcctgcc ccgaattcac gaggctgagg    300
catccgggag ctggcgtaat gcctggccgc agtgtgtgtg tatccgatac cccactctgg    360
aaggaaccat ccagtaaagg tctttcagaa ccactaaggt cccagccctc actaggatgt    420
caggagccag gtctaggccc agctttcaca ctgtggcagc ccagtgaagc agactgggcc    480
atgaactctc ctagccctgg ggccagcctg ttccacaggc accctgcag gaggcgctgc     540
caggagagcc ttccatctcg gggctctttg aggttccctc cttctgggtg ttcttcaggc    600
tgagcagaga ggctcctgta ccctctctct cggaatctga agagccagat ttaggccggg    660
caaaggggct caccctata atcccaggac tttgggaggc caaggcagga ggatcacttg     720
agtccagaaa ttcaagaccc gcctgggcat cataatgaga ccccatctct acaacaaaat    780
ttaataaatt agctgggcac agtgttcaca cctgtagtcc cggccactcg gggctgaggc    840
aggaggatca ctggaacctg ggaggttgcc actgcaaaaa aaaaaaaaaa aaaaaaaaa    900
aaaaaaaaaa aaaaaaaaaa aaaaa                                         925

<210> SEQ ID NO 21
<211> LENGTH: 849
<212> TYPE: DNA
<213> ORGANISM: Homo sapiens

<400> SEQUENCE: 21
acagttgctt tgaggcagta ccggaggaga aagatggcgg ctaccttact agctgctcgg     60
ggagccgggc cagcaccggc ttggggggccg gaggcgttca ctccagactg gaaagccga    120
gaagtttcca ctgggaccac tatcatggcc gtgcagtttg acggggggcgt ggttctgggg    180
gcggactcca gaacaaccac tgggtcctac atcgccaatc gagtgactga caagctgaca    240
cctattcacg accgcatttt ctgctgtcgc tcaggctcag ctgctgatac ccaggcagta    300
gctgatgctg tcacctacca gctcggtttc cacagcattg aactgaatga gcctccactg    360
gtccacacag cagccagcct cttaaggag atgtgttacc gataccggga agacctgatg    420
gcgggaatca tcatcgcagg ctgggaccct caagaaggag ggcaggtgta ctcagtgcct    480
atgggggggta tgatggtaag gcagtccttt gccattggag gctccgggag ctcctacatc    540
tatggctatg ttgatgctac ctaccgggaa ggcatgacca aggaagagtg tctgcaattc    600
actgccaatg ctctcgcttt ggccatggag cgggatggct ccagtggagg agtgatccgc    660
ctggcagcca ttgcagagtc aggggtagag cggcaagtac ttttgggaga ccagataccc    720
aaattcgccg ttgccacttt accacccgcc tgaatcctgg gattctagta tgcaataaga    780
gatgccctgt actgatgcaa aatttaataa agtttgtcac agagaaaaaa aaaaaaaaaa    840
aaaaaaaaa                                                           849

<210> SEQ ID NO 22
<211> LENGTH: 4142
<212> TYPE: DNA
<213> ORGANISM: Homo sapiens

<400> SEQUENCE: 22
atatgacaga tacctagcat ctagcaaaat aatggcagct gcttaccttg accccaactt     60
gaatcacaca ccaaattcga gtactaagac tcacctgggt actggtatgg aacgttctcc    120
tggtgcaatg gagcgagtat taaaggtctt tcattatttt gaaagcaata gtgagccaac    180
```

```
cacctgggcc agtattatca ggcatggaga tgctactgat gtcagggca tcattcagaa      240 gatagtggac agtcacaaag taaagcatgt ggcctgctat ggattccgcc tcagtcacct      300
gcggtcagag gaggttcact ggcttcacgt ggatatgggc gtctccagtg tgagggagaa      360
gtatgagctt gctcacccac cagaggagtg gaaatatgaa ttgagaattc gttatttgcc      420
aaaaggattt ctaaaccagt ttactgaaga taagccaact ttgaatttct tctatcaaca      480
ggtgaagagc gattatatgt tagagatagc tgatcaagtg gaccaggaaa ttgctttgaa      540
gttgggttgt ctagaaatac ggcgatcata ctgggagatg cggggcaatg cactagaaaa      600
gaagtctaac tatgaagtat tagaaaaaga tgttggttta aagcgatttt ttcctaagag      660
tttactggat tctgtcaagg ccaaaacact aagaaaactg atccaacaaa catttagaca      720
atttgccaac cttaatagag aagaaagtat tctgaaattc tttgagatcc tgtctccagt      780
ctacagattt gataaggaat gcttcaagtg tgctcttggt tcaagctgga ttatttcagt      840
ggaactggca atcggcccag aagaaggaat cagttaccta acggacaagg ctgcaatcc       900 cacacatctt gctgacttca ctcaagtgca aaccattcag tattcaaaca gtgaagacaa      960
ggacagaaaa ggaatgctac aactaaaaat agcaggtgca cccgagcctc tgacagtgac     1020
ggcaccatcc ctaaccattg cggagaatat ggctgaccta atagatgggt actgccggct     1080
ggtgaatgga acctcgcagt catttatcat cagacctcag aaagaaggtg aacgggcttt     1140
gccatcaata ccaaagttgg ccaacagcga aaagcaaggc atgcggacac acgccgtctc     1200
tgtgtcagaa acagatgatt atgctgagat tatagatgaa gaagatactt acaccatgcc     1260
ctcaaccagg gattatgaga ttcaaagaga aagaatagaa cttggacgat gtattggaga     1320
aggccaattt ggagatgtac atcaaggcat ttatatgagt ccagaaatc cagctttggc      1380 ggttgcaatt aaaacatgta aaaactgtac ttcggacagc gtgagagaga aatttcttca     1440
agaagcctta acaatgcgtc agtttgacca tcctcatatt gtgaagctga ttggagtcat     1500
cacagagaat cctgtctgga taatcatgga gctgtgcaca cttggagagc tgaggtcatt     1560
tttgcaagta aggaaataca gtttggatct agcatctttg atcctgtatg cctatcagct     1620
tagtacagct cttgcatatc tagagagcaa aagatttgta cacagggaca ttgctgctcg     1680
gaatgttctg gtgtcctcaa atgattgtgt aaaattagga gactttggat tatcccgata     1740 tatgaagat agtacttact acaaagcttc caaggaaaa ttgcctatta atggatggc        1800 tccagagtca atcaattttc gacgttttac ctcagctagt gacgtatgga tgtttggtgt     1860
gtgtatgtgg gagatactga tgcatggtgt gaagcctttt caaggagtga agaacaatga     1920
tgtaatcggt cgaattgaaa atgggaaag attaccaatg cctccaaatt gtcctcctac      1980
cctctacagc cttatgacga aatgctgggc ctatgacccc agcaggcggc ccaggtttac     2040
tgaacttaaa gctcagctca gcacaatcct ggaggaagag aaggctcagc aagaagagcg     2100
catgaggatg gagtccagaa gacaggccac agtgtcctgg gactccggag ggtctgatga     2160
agcaccgccc aagcccagca gaccgggtta tcccagtccg aggtccagcg aaggattta      2220 tcccagccca cagcacatgg tacaaaccaa tcattaccag gactctacag tattggacct     2280
gcgagggatt gggcaagtgt tgccaaccca tctgatggaa gagcgtctaa tccgacagca     2340
acaggaaatg gaagaagatc agcgctggct ggaaaaagag aaagatttc tgaaacctga     2400 tgtgagactc tctcgaggca gtattgacag ggaggatgga agtcttcagg gtccgattgg     2460
aaaccaacat atatatcagc ctgtgggtaa accagatcct gcagctccac caaagaaacc     2520
```

```
gcctcgccct ggagctcccg gtcatctggg aagccttgcc agcctcagca gccctgctga    2580
cagctacaac gagggtgtca agcttcagcc ccaggaaatc agccccctc ctactgccaa     2640 cctggaccgg tcgaatgata aggtgtacga gaatgtgacg ggcctggtga aagctgtcat    2700
cgagatgtcc agtaaaatcc agccagcccc accagaggag tatgtcccta tggtgaagga   2760
agtcggcttg gccctgagga cattattggc cactgtggat gagaccattc ccctcctacc   2820
agccagcacc caccgagaga ttgagatggc acagaagcta ttgaactctg acctgggtga   2880
gctcatcaac aagatgaaac tggcccagca gtatgtcatg accagcctcc agcaagagta   2940
caaaaagcaa atgctgactg ctgctcacgc cctggctgtg gatgccaaaa acttactcga   3000
tgtcattgac caagcaagac tgaaaatgct tgggcagacg agaccacact gagcctcccc   3060
taggagcacg tcttgctacc ctcttttgaa gatgttctct agccttccac cagcagcgag   3120
gaattaaccc tgtgtcctca gtcgccagca cttacagctc caacttttt gaatgaccat    3180 ctggttgaaa atctttctc atataagttt aaccacactt tgatttgggt tcattttttg    3240
ttttgttttt ttcaatcatg atattcagaa aaatccagga tccaaaatgt ggcgtttttc   3300
taagaatgaa aattatatgt aagcttttaa gcatcatgaa gaacaattta tgttcacatt   3360
aagatacgtt ctaaaggggg atggccaagg ggtgacatct taattcctaa actaccttag   3420
ctgcatagtg gaagaggaga gcatgaagca aagaattcca ggaaacccaa gaggctgaga   3480
attcttttgt ctaccataga attattatcc agactgaat ttttgtttgt tagaacaccc    3540
ttcagttgca atatgctaat cccactttac aaagaatata aaagctatat tttgaagact   3600
tgagttattt cagaaaaaac tacagccctt tttgtcttac ctgcctttta ctttcgtgtg   3660
gatatgtgaa gcattgggtc gggaactagc tgtagaacac aactaaaaac tcatgtcttt   3720
tttcacagaa taatgtgcca gttttttgta gcaatgatat ttctcttgga agcagaaatg   3780
ctttgtacca gagcacctcc aaactgcatt gaggagaagt tccagaacca tccccttttt   3840
ccatttttat ataatttata aagaaagatt aaagccatgt tgactatttt acagccactg   3900
gagttaacta acccttcctt gtatctgtct tcccaggaga gaatgaagca aaacaggaat   3960
ttggttttct tttgatgtcc agttacacca tccattctgt taattttgaa aaaatatacc   4020 ctcccttag tttgttgggg gatataaatt attctcagga agaatataat gaactgtaca    4080
gttactttga cctattaaaa aggtgttacc agtaaagttc ttgttgtaaa aaaaaaaaa    4140 aa                                                                  4142

<210> SEQ ID NO 23
<211> LENGTH: 2594
<212> TYPE: DNA
<213> ORGANISM: Homo sapiens

<400> SEQUENCE: 23 agggggccgcg gagccgcggc taaggaacgc gggccgccca cccgctcccg gtgcagcggc     60
ctccgcgccg ggttttggcg cctccgcgg gcgcccccct cctcacggcg agcgctgcca     120
cgtcagacga agggcgcagc gagcgtcctg atccttccgc ccggacgctc aggacagcgg    180
cccgctgctc ataagactcg gccttagaac cccagtatca gcagaaggac attttaggac    240
gggacttggg tgactctagg gcactggttt tctttccaga gagcggaaca ggcgaggaaa    300
agtagtccct tctcggcgat tctgcggagg atctccgtg gggcggtgaa cgccgatgat    360
tatataagga cgcgccgggt gtggcacagc tagttccgtc gcagccggga tttgggtcgc   420
agttcttgtt tgtggatcgc tgtgatcgtc acttgacaat gcagatcttc gtgaagactc    480
```

```
tgactggtaa gaccatcacc ctcgaggttg agcccagtga caccatcgag aatgtcaagg      540
caaagatcca agataaggaa ggcatccctc ctgaccagca gaggctgatc tttgctggaa      600
aacagctgga agatgggcgc accctgtctg actacaacat ccagaaagag tccaccctgc      660
acctggtgct ccgtctcaga ggtgggatgc aaatcttcgt gaagacactc actggcaaga      720
ccatcaccct tgaggtcgag cccagtgaca ccatcgagaa cgtcaaagca agatccagg       780 acaaggaagg cattcctcct gaccagcaga ggttgatctt tgccggaaag cagctggaag      840
atgggcgcac cctgtctgac tacaacatcc agaaagagtc taccctgcac ctggtgctcc      900
gtctcagagg tgggatgcag atcttcgtga agaccctgac tggtaagacc atcaccctcg      960
aggtggagcc cagtgacacc atcgagaatg tcaaggcaaa gatccaagat aaggaaggca      1020
ttccttctga tcagcagagg ttgatctttg ccggaaaaca gctggaagat ggtcgtaccc      1080
tgtctgacta caacatccag aaagagtcca ccttgcacct ggtactccgt ctcagaggtg      1140
ggatgcaaat cttcgtgaag acactcactg gcaagaccat cacccttgag gtcgagccca      1200
gtgacactat cgagaacgtc aaagcaaaga tccaagacaa ggaaggcatt cctcctgacc      1260
agcagaggtt gatctttgcc ggaaagcagc tggaagatgg gcgcaccctg tctgactaca      1320
acatccagaa agagtctacc ctgcacctgg tgctccgtct cagaggtggg atgcagatct      1380
tcgtgaagac cctgactggt aagaccatca ctctcgaagt ggagccgagt gacaccattg      1440
agaatgtcaa ggcaaagatc caagacaagg aaggcatccc tcctgaccag cagaggttga      1500
tctttgccgg aaaacagctg gaagatggtc gtaccctgtc tgactacaac atccagaaag      1560
agtccacctt gcacctggtg ctccgtctca gaggtgggat gcagatcttc gtgaagaccc      1620
tgactggtaa gaccatcact ctcgaggtgg agccgagtga caccattgag aatgtcaagg      1680
caaagatcca agacaaggaa ggcatccctc ctgaccagca gaggttgatc tttgctggga      1740
aacagctgga agatggacgc accctgtctg actacaacat ccagaaagag tccaccctgc      1800
acctggtgct ccgtcttaga ggtgggatgc agatcttcgt gaagaccctg actggtaaga      1860
ccatcactct cgaagtggag ccgagtgaca ccattgagaa tgtcaaggca agatccaag        1920 acaaggaagg catccctcct gaccagcaga ggttgatctt tgctgggaaa cagctggaag      1980
atggacgcac cctgtctgac tacaacatcc agaaagagtc caccctgcac ctggtgctcc      2040
gtcttagagg tgggatgcag atcttcgtga agaccctgac tggtaagacc atcactctcg      2100
aagtggagcc gagtgacacc attgagaatg tcaaggcaaa gatccaagac aaggaaggca      2160
tccctcctga ccagcagagg ttgatctttg ctgggaaaca gctggaagat ggacgcaccc      2220
tgtctgacta caacatccag aaagagtcca cctgcacct ggtgctccgt ctcagaggtg       2280
ggatgcaaat cttcgtgaag accctgactg gtaagaccat caccctcgag gtggagccca      2340
gtgacaccat cgagaatgtc aaggcaaaga tccaagataa ggaaggcatc cctcctgatc      2400
agcagaggtt gatctttgct gggaaacagc tggaagatgg acgcaccctg tctgactaca      2460
acatccagaa agagtccact ctgcacttgg tcctgcgctt gagggggggt gtctaagttt      2520
ccccttttaa ggtttcaaca aatttcattg cactttcctt tcaataaagt tgttgcattc      2580
ccaaaaaaaa aaaa                                                        2594
```